(12) United States Patent
Mizuno et al.

(10) Patent No.: US 6,294,677 B1
(45) Date of Patent: Sep. 25, 2001

(54) THIOPYRAN DERIVATIVES

(75) Inventors: Akira Mizuno, Kyoto; Makoto Shibata, Ashikaga; Tomoe Iwamori, Ibaraki; Norio Inomata, Mino, all of (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/531,141

(22) Filed: Mar. 17, 2000

(30) Foreign Application Priority Data

Jun. 23, 1995 (JP) ................................ 7-179701

(51) Int. Cl.[7] ............ C07D 335/06; C07D 495/10; C07D 497/10; C07D 409/06; A61K 31/496
(52) U.S. Cl. ................. 549/17; 549/23; 549/27
(58) Field of Search ................. 549/23, 27, 17

(56) References Cited

U.S. PATENT DOCUMENTS

| | | | |
|---|---|---|---|
| 4,788,290 | 11/1988 | Stack | 544/357 |
| 5,874,429 | 2/1999 | Mizuno et al. | 514/226.5 |
| 5,977,111 | 11/1999 | Mizuno et al. | 514/253 |

FOREIGN PATENT DOCUMENTS

| | | |
|---|---|---|
| 0 389 425 | 9/1990 | (EP) . |
| 0 433 149 | 6/1991 | (EP) . |
| 0 457 586 | 11/1991 | (EP) . |
| 0 543 497 | 5/1993 | (EP) . |
| 0 558 245 | 9/1993 | (EP) . |

OTHER PUBLICATIONS

Bargagna, et al., *Chemical Abstracts*, vol. 114, No. 23819 (1991).
Debernardis, et al., *Chemical Abstracts*, vol. 125, No. 114706 (1996).
Debernardis, et al., *Chemical Abstracts*, vol. 125, No. 142771 (1996).
Malleron, J., et al., "New Indole Derivatives As Potent And Selective Serotonin Uptake Inhibitors," *J. Med. Chem.*, vol. 36, pp. 1194–1202 (1993).
Sano, et al., *Chemical Abstracts*, vol. 117, No. 150893 (1992).
Saxena, "Serotonin Receptors: Subtypes, Functional Responses and Therapeutic Relevance," *Pharma. Ther.*, vol. 66, pp. 339–368 (1995).
Leonardi, et al., Hungarian Patent Application publish under No. T/72448, 1986 (Abstract).
Leonardi, et al., *Chemical Abstract*, vol. 120, No. 106770, 1994 (Abstract for EP 558 245).
Baldwin, et al., *Chemical Abstracts*, vol. 117, No. 48533, 1992 (Abstract for EP 457 586).
Baldwin, et al., *Chemical Abstracts*, vol. 119, No. 225934, 1993 (Abstract for EP 543 497).
Watanabe, et al., "Synthesis and 5–$HT_2$ Antagonist Activity of Bicyclic 1,2,4–Triazol–3(2H)–one and 1,3,5–Triazine 2,4 (3H)–Dione Derivatives", *J. Med. Chem.*, vol. 35, pp. 189–194 (1992).
Cushing, et al., *Cardiovascular & Renal–Overview*, pp. 569–579 (1993).
Comte, et al. *Chemical Abstracts*, vol. 115, No. 183316, 1991 (Abstract for EP 433,149).
Hutchinson, A., *Chemical Abstracts*, vol. 114, No. 122062, 1991 (Abstract for EP 389,425).

*Primary Examiner*—Mark L. Berch
*Assistant Examiner*—Kahsay Habte
(74) *Attorney, Agent, or Firm*—Oblon, Spivak, McClelland, Maier & Neustadt, P.C.

(57) ABSTRACT

An intermediate represented by the following formula (XVIII), (XVIII)

wherein A is a sulfur atom or the group —CH=CH—; L is an alkylene group which may be substituted, an alkenylene group which may be substituted, or an alkynylene group which may be substituted; W represents a leaving group selected from the group consisting of a halogen atom, an alkyl sulfonyloxy group, and an aryl sulfonyloxy group, and Z represents the group;

(wherein $R_1$ is an alkyl group which may be substituted, an aromatic carbocyclic group which may be substituted, or an aralkyl group which may be substituted, $X_1$, $X_2$, and $X_3$ individually represent an oxygen atom or a sulfur atom, and G represents an ethylene group or a trimethylene group, of which one or more hydrogen atoms of the ethylene group or trimethylene group may be replaced by a halogen atom, alkyl group, aromatic carbocyclic group, aralkyl group, or alkylidene group).

2 Claims, No Drawings

US 6,294,677 B1

THIOPYRAN DERIVATIVES

BACKGROUND OF THE INVENTION

1. Field of the Invention:

The present invention relates to novel thiopyran derivatives. More specifically, this invention is concerned with benzothiopyran derivatives, thienothiopyran derivatives and salts thereof, said derivatives and salts being useful for the prevention or treatment of ischemic heart diseases such as angina pectoris, arrhythmia, myocardial infarction, congestive heart failure and post PTCA restenosis, cerebrovascular disturbances such as cerebral infarction and cerebral sequelae after subarachnoid hemorrhage, peripheral circulatory disturbance such as arteriosclerosis obliterans, thromboangina oblite, Raynaud disease, Buerger disease, and/or hypertension; their preparation processes; and pharmaceuticals comprising them as effective ingredients.

2. Discussion of the Background

Serotonin is a compound contained abundantly in platelets, which are a blood component, and in a central nervous system, it acts as a neurotransmitter. In platelets, it is released upon stimulation by thromboxane $A_2$, ADP, collagen or the like and synergistically acts on various platelet aggregation factors or vasoconstrictors through activation of serotonin-2 receptors in the platelets and vascular smooth muscle cells, thereby inducing strong platelet aggregation and vasoconstriction [P. M. Vanhoutte, "Journal of Cardiovascular Pharmacology", Vol. 17 (Supple. 5), S6–S12 (1991)].

Serotonin is also known to potentiate proliferation of vascular smooth muscle cells [S. Araki et al., "Atherosclerosis", Vol. 83, p29–p34(1990)]. It has been considered that, particularly when endothelial cells are injured as in arteriosclerosis or myocardial infarction, the vasoconstricting action and thrombus forming action of serotonin are exasperated, thereby reducing or even stopping blood supply to myocardial, cerebral and peripheral organs [P. Golino et al., "The New England Journal of Medicine", Vol. 324, No. 10, p641–p648 (1991), Y. Takiguchi et al., "Thrombosis and Haemostasis", Vol. 68(4), p460–p463 (1992), A. S. Weyrich et al., "American Journal of Physiology", Vol. 263, H349–H358 (1992)].

Being attracted by such actions of serotonin or serotonin-2 receptors, various attempts are now under way to use a serotonin-2 receptor antagonist as a pharmaceutical for ischemic diseases of the heart, the brain and peripheral tissues.

Several compounds such as sarpogrerate are known to possess the serotonin-2-receptor antagonistic action. These compounds still exhibit many problems to be solved, such as the intensity of the activity, toxicity, and side effects. A drug exhibiting both the anti-serotonin action and the $\alpha_1$ blocking action has a possibility of alleviating side effects such as orthostatic hypotension and reflex pulsus frequens which involve antihypertensive action due to the $\alpha_1$ blocking action. In addition, because hypertension is a major risk factor in ischemic heart diseases, the drug exhibiting both the anti-serotonin action and the $\alpha_1$ blocking action has the potential of being extremely effective for the treatment and prevention of hypertension and ischemic heart diseases.

In view of this situation, the inventors of the present invention have undertaken extensive studies and discovered thiopyran derivatives exhibiting a strong serotonin-2-recepter antagonistic action and useful as a drug for preventing or treating ischemic heart diseases, cerebrovascular disturbance, and peripheral circulatory disturbance, with minimal toxic or side effects. In addition, some of the compounds among the thiopyran derivatives were found to also possess the $\alpha_1$ blocking action and are thus useful as antihypertensive agents with less side effects, and can therefore be widely used in the treatment and prevention of circulatory diseases.

SUMMARY OF THE INVENTION

Accordingly, an object of the present invention is to provide a thiopyran derivative or the salt thereof represented by the following formula (I) or (I'),

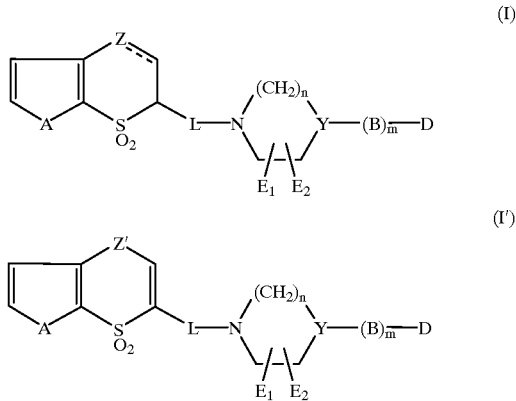

wherein,
  A represents a sulfur atom or the group —CH=CH—;
  the dotted line indicates that the bond may be either present or absent;
  when the dotted line indicates that the bond is present, Z represents the group,

and when the dotted line indicates that the bond is absent, Z represents one of the following groups,

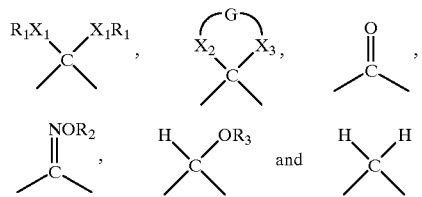

(wherein $R_1$ is an alkyl group which may be substituted, an aryl group which may be substituted, or an aralkyl group which may be substituted, $R_2$ is a hydrogen atom, an alkyl group which may be substituted, an aryl group which may be substituted, or an aralkyl group which may be substituted, $R_3$ is a hydrogen atom, an alkyl group which may be substituted, or an aralkyl group which may be substituted, $X_1$, $X_2$, and $X_3$ individually represent an oxygen atom or a sulfur atom, and G represents an ethylene group, of which one or more hydrogen atoms may be replaced by a halogen atom, alkyl group, aryl group, aralkyl group, or alkylidene group, or a trimethylene group, of which one or more hydrogen atoms may be replaced by a halogen atom, alkyl group, aryl group, aralkyl group, or alkylidene group);

Z' represents the group;

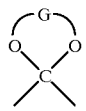

(wherein G has the same meaning as defined above);

L is an alkylene group which may be substituted, an alkenylene group which may be substituted, or an alkynylene group which may be substituted;

Y represents the group CH, the group C=, or a nitrogen atom;

when Y is the group CH, m is 0 or 1, n is 1 or 2, and B is an oxygen atom, a sulfur atom, a carbonyl group, a sulfinyl group, a sulfonyl group, an alkylene group, an alkenylene group, a hydroxymethylene group which may be substituted, a group —$CHR_4$— (wherein $R_4$ is an alkyl group which may be substituted, an aryl group which may be substituted, or an aralkyl group which may be substituted), or a cyclic or acyclic acetal group which may be substituted;

when Y is the group C=, m is 1, n is 1 or 2, and B is the group,

(wherein the double bond is linked to Y and $R_5$ is an alkyl group which may be substituted, an aryl group which may be substituted, or an aralkyl group which may be substituted); and when Y is a nitrogen atom, m is 0 or 1, n is 2 or 3, and B is a carbonyl group, a sulfonyl group, an alkylene group, an alkenylene group, or a group —$CHR_6$— (wherein $R_6$ is an alkyl group which may be substituted, an aryl group which may be substituted, or an aralkyl group which may be substituted);

$E_1$ and $E_2$ individually represent a hydrogen atom or a lower alkyl group; and D represents an aromatic hydrocarbon group which may be substituted or an aromatic heterocyclic group which may be substituted.

Another object of the present invention is to provide a process for preparing said thiopyran derivative (I) or (I'), or the salt thereof.

Still another object of the present invention is to provide a drug composition for circulatory diseases comprising said thiopyran derivative (I) or (I'), or a pharmaceutically acceptable salt thereof, as an effective component.

Other objects, features and advantages of the invention will hereinafter become more readily apparent from the following description.

DETAILED DESCRIPTION OF THE INVENTION AND PREFERRED EMBODIMENTS

In the thiopyran derivative (I) or (I') of the present invention, given as preferred examples of $R_1$ are alkyl group having 1 to 4 carbon atoms which may be branched, such as methyl or ethyl; aryl groups having 6 to 14 carbon atoms such as phenyl or naphthyl; and aralkyl groups having 7 to 22 carbon atoms such as benzyl or phenethyl. These groups may be substituted by one or more of a halogen atom such as fluorine, chlorine, or bromine; an alkyl group having preferably 1 to 4 carbon atoms, such as methyl or ethyl; or an alkoxy group having preferably 1 to 4 carbon atoms such as methoxy or ethoxy. In this instance, as preferred examples of the group $R_1X_1$, such groups as methoxy, methylthio, ethoxy, and ethylthio are given.

The following groups,

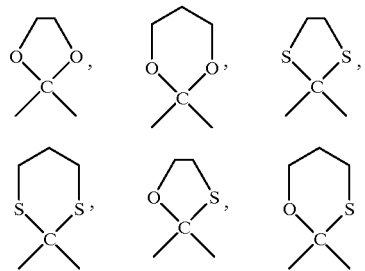

are given as preferred examples of the group,

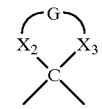

One or more hydrogens of the above groups may be replaced by a halogen atom such as fluorine, chlorine, or bromine; an alkyl group having preferably 1 to 4 carbon atoms, such as methyl or ethyl; an aryl group having preferably 6 to 14 carbon atoms, such as phenyl or naphthyl; an aralkyl group having preferably 7 to 22 carbon atoms, such as benzyl or phenethyl; or an alkylidene group having preferably 1 to 4 carbon atoms, such as methylidene or ethylidene.

In the group =$NOR_2$, given as preferred examples of $R_2$ are hydrogen; alkyl groups having 1 to 4 carbon atoms which may be branched, such as methyl or ethyl; aryl groups having 6 to 14 carbon atoms such as phenyl or naphthyl; and aralkyl groups having 7 to 22 carbon atoms such as benzyl or phenethyl. These groups may be substituted by one or more halogen atoms such as fluorine, chlorine, or bromine; alkyl groups having preferably 1 to 4 carbon atoms, such as methyl or ethyl; or alkoxy groups having preferably 1 to 4 carbon atoms such as methoxy or ethoxy.

Given as preferred examples of $R_3$ are hydrogen; alkyl groups having 1 to 4 carbon atoms which may be branched, such as methyl or ethyl; and aralkyl groups having 7 to 22 carbon atoms such as benzyl or phenethyl. These groups may be substituted by one or more halogen atoms such as fluorine, chlorine, or bromine; alkyl groups having preferably 1 to 4 carbon atoms, such as methyl or ethyl; or alkoxy groups having preferably 1 to 4 carbon atoms such as methoxy or ethoxy.

The following groups,

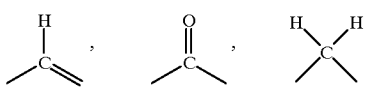

are also included as preferred examples of Z.
The following groups are given as particularly preferred examples of Z,

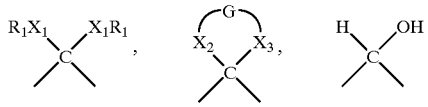

wherein G, $R_1$, $X_1$, $X_2$, and $X_3$ are the same meanings as defined above.

Given as preferred examples of L are alkylene groups having 2 to 10 carbon atoms which may be branched, such as ethylene, trimethylene, tetramethylene, pentamethylene, or octamethylene; alkenylene groups having 4 to 10 carbon atoms which may be branched, such as 2-buthenylene or 3-pentenylene; and alkynylene groups having 4 to 10 carbon atoms which may be branched, such as 2-butynylene or 3-pentynylene. These groups may be substituted by one or more halogen atoms such as fluorine, chlorine, or bromine. Among these groups, ethylene, trimethylene, and tetramethylene are particularly preferred.

In the thiopyran derivative (I) or (I'), the following group,

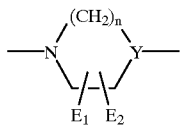

(wherein $E_1$, $E_2$, Y and n are the same meanings as defined above), is a heterocyclic group derived from pyrrolidine, piperidine, piperazine, or homopiperazine, wherein two or less hydrogen atoms on the ring may be replaced by an alkyl group having preferably 1 to 4 carbon atoms such as methyl or ethyl.

When the above group is a heterocyclic group derived from pyrrolidine or piperidine, preferably when this group is piperidine, m is 0 or 1 (when Y is C=, m is 1) and B is an oxygen atom, a sulfur atom, a carbonyl group, a sulfinyl group, a sulfonyl group, an alkylene group (an alkylene group preferably having 1 to 4 carbon atoms, particularly preferably methylene), an alkenylene group (an alkenylene group preferably having 2 to 5 carbon atoms, particularly preferably 2-propenylene), a hydroxymethylene group which may be substituted, a group —CHR$_4$— (wherein R$_4$ is an alkyl group which may be substituted and preferably having 1 to 4 carbon atoms such as methyl or ethyl, an aryl group which may be substituted and preferably having 6 to 14 carbon atoms such as phenyl or naphthyl, or an aralkyl group which may be substituted and preferably having 7 to 22 carbon atoms such as benzyl or phenethyl), a group,

(wherein the double bond is linked to Y and $R_5$ is an alkyl group which may be substituted and preferably having 1 to 4 carbon atoms such as methyl or ethyl, an aryl group which may be substituted and preferably having 6 to 14 carbon atoms such as phenyl or naphthyl, or an aralkyl group which may be substituted and preferably having 7 to 22 carbon atoms such as benzyl or phenethyl), or a cyclic or acyclic acetal group of which one or more hydrogens may be replaced by other groups.

The following groups are given as examples of the cyclic or acyclic acetal group.

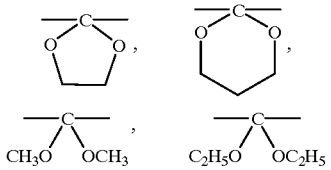

Given as preferred examples of the substituent for the hydroxymethylene group in the group B are an alkyl group preferably having 1 to 4 carbon atoms such as methyl or ethyl and an aryl group preferably having 6 to 14 carbon atoms such as phenyl or naphthyl, which are present bonded with the carbon atom of the methylene group. These substituents for the hydroxymethylene group may be replaced by one or more hydroxyl groups, halogen atoms such as fluorine, chlorine, or bromine, or alkoxy groups having preferably 1 to 4 carbon atoms such as methoxy or ethoxy.

Particularly preferred examples of the hydroxymethylene group which may be substituted include hydroxymethylene group with no substituents or with substituents such as phenyl, fluorophenyl, or hydroxyphenyl.

Further, given as examples of substituents for $R_4$ are one or more halogen atoms such as fluorine, chlorine, or bromine, alkyl groups having preferably 1 to 4 carbon atoms such as methyl or ethyl, and alkoxy groups having preferably 1 to 4 carbon atoms such as methoxy or ethoxy.

Further, given as examples of substituents for $R_5$ are one or more halogen atoms such as fluorine, chlorine, or bromine, alkyl groups having preferably 1 to 4 carbon atoms such as methyl or ethyl, alkoxy groups having preferably 1 to 4 carbon atoms such as methoxy or ethoxy, and hydroxyl groups. Given as examples of substituents for the cyclic or acyclic acetal group are one or more of halogen atoms such as fluorine, chlorine, or bromine, alkyl groups having preferably 1 to 4 carbon atoms such as methyl or ethyl, aryl groups having preferably 6 to 14 carbon atoms such as phenyl or naphthyl, aralkyl groups having preferably 7 to 22 carbon atoms such as benzyl or phenethyl, and alkylidene groups having preferably 1 to 4 carbon atoms such as methylidene or ethylidene.

Among these groups for B, the carbonyl group is particularly preferred.

When the above heterocyclic group is a group derived from piperazine or homopiperazine, preferably when this group is piperazine, m is 0 or 1 (preferably 0) and B is a carbonyl group, a sulfonyl group, an alkylene group (an alkylene group preferably having 1 to 4 carbon atoms, particularly preferably methylene), an alkenylene group (an alkenylene group preferably having 3 to 6 carbon atoms, particularly preferably 2-propenylene), or a group —CHR$_6$— (wherein R$_6$ is an alkyl group preferably having 1 to 4 carbon atoms such as methyl or ethyl, an aryl group preferably having 6 to 14 carbon atoms such as phenyl or naphthyl, or an aralkyl group preferably having 7 to 22 carbon atoms such as benzyl or phenethyl).

$R_6$ may be substitued by one or more of halogen atoms such as fluorine, chlorine, or bromine, alkyl groups having preferably 1 to 4 carbon atoms such as methyl or ethyl, or alkoxy groups having preferably 1 to 4 carbon atoms such as methoxy or ethoxy.

Among these groups for B, the phenylmethylene group which may be substituted is preferred.

Preferred examples of D in the formulas (I) or (I') are aromatic hydrocarbon groups having preferably 6 to 28 carbon atoms such as a phenyl group of which one or more hydrogen atoms may be substituted by other groups or naphthyl group of which one or more hydrogen atoms may be substituted by other groups. Also included in other preferred examples of D are mono- or bi-cyclic aromatic heterocyclic groups containing 3 or less oxygen, sulfur, and/or nitrogen atoms, such as pyridyl, pyrimidyl, benzisothiazolyl, benzisoxazolyl, indazolyl, and indolyl, of which one or more hydrogen atoms may be substituted by other groups.

Given as examples of substituents for the above aromatic hydrocarbon groups or aromatic heterocyclic groups are halogen atoms such as fluorine, chlorine, or bromine; alkyl groups having preferably 1 to 4 carbon atoms such as methyl or ethyl; aryl groups having preferably 6 to 14 carbon atoms such as phenyl or naphthyl; aralkyl groups having preferably 7 to 22 carbon atoms such as benzyl or phenethyl; aralkyloxy groups having preferably 7 to 22 carbon atoms such as benzyloxy; cyano group; nitro group; carboxyl group; alkoxycarbonyl groups (the alcohol portion having 1 to 6 carbon atoms); lower-alkyl sulfonylamino groups (the alkyl portion having 1 to 4 carbon atoms); carbamoyl group; and hydroxyl group.

Preferred groups among these groups for D are a phenyl group unsubstituted or substituted by halogen, alkoxy group, or hydroxyl group; a benzisothiazolyl group unsubstituted or substituted by halogen; a benzisooxazolyl group unsubstituted or substituted by halogen; and an indazolyl group unsubstituted or substituted by halogen. Particularly preferred are a phenyl group and phenyl groups substituted by fluorine, methoxy group, or hydroxy group.

Many compounds of the present invention of the formula (I) or (I') include isomers. Any and all these isomers and mixtures of isomers are included in the present invention.

The thiopyran derivatives (I) and (I') of the present invention can be prepared by various processes. Some examples of preferred processes are as follows. <Processes 1>

Among the thiopyran derivatives (I), the compound (Ia) having the following group,

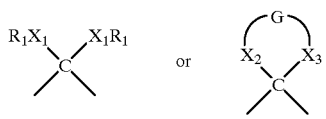

(wherein G, $R_1$, $X_1$, $X_2$, and $X_3$ have the same meanings as defined above) for Z in the formula (I) can be prepared by one of the following processes.

Process 1A: The compound (Ia) can be prepared by converting a compound of the formula (II) into a compound of the formula (IV) by reacting a compound of the formula (III), and reacting the compound of the formula (IV) and a nitrogen-containing compound of the formula (V) or a salt thereof according to the following reaction scheme.

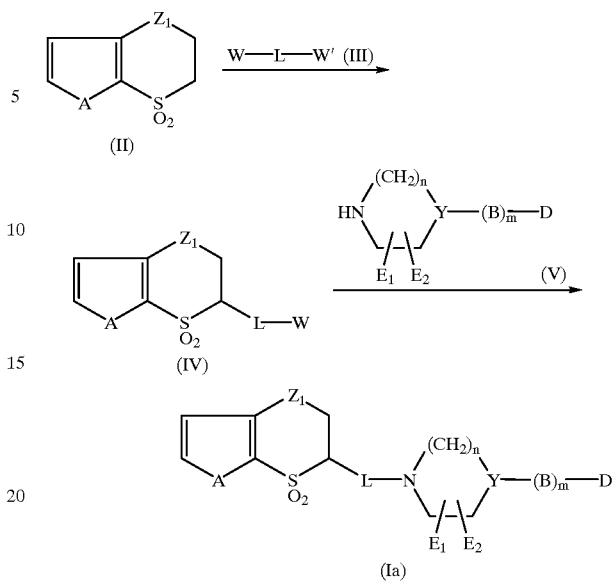

wherein A, B, D, $E_1$, $E_2$, L, Y, m, and n have the same meanings as defined above, and $Z_1$ is the group,

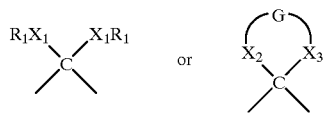

(wherein G, $R_1$, $X_1$, $X_2$, and $X_3$ have the same meanings as defined above), and W and W' individually indicate a leaving group.

In the above reactions, the conversion of the compound (II) into the compound (IV) is carried out by treating the compound (II) with an inorganic or organic base and then reacting with the compound (III).

W and W' in the compound (III) are leaving groups and include a halogen atom such as chlorine or bromine, an alkyl sulfonyloxy group such as methanesulfonyloxy group, and an aryl sulfonyloxy group such as p-toluenesulfonyloxy group.

As examples of the inorganic or organic base, potassium hydroxide, sodium bis(trimethylsilyl) amide, n-butyl lithium, lithium di-isopropyl amide, and potassium t-butoxide are given. Further, diethyl ether, tetrahydrofuran, dioxane, and toluene are given as examples of the solvents used in this reaction, which is preferably carried out at a temperature of from −78° C. to room temperature.

To prepare the compound (Ia) by reacting the resulting compound (IV) and a nitrogen-containing compound (V), this compound (IV) is reacted with the nitrogen-containing compound (V) or an organic or inorganic acid salt of the nitrogen-containing compound in the above-mentioned solvent or other solvent such as methanol, ethanol, dimethylformamide, dimethylsulfoxide, acetonitrile, acetone, or 2-butanone, optionally together with an organic base such as triethylamine, pyridine, collidine, or potassium t-butoxide or an inorganic base such as potassium carbonate, sodium carbonate, sodium hydrogen carbonate, sodium hydroxide, or sodium hydride, and a further optional addition of alkaline iodide such as potassium iodide or sodium iodide at a temperature from 0° C. to 150° C.

Enumerated as examples of the nitrogen-containing compound (V) are 1-phenylpiperazine, 1-(2-fluorophenyl)

piperazine, 1-(3-fluorophenyl)piperazine, 1-(4-fluorophenyl)piperazine, 1-(4hydroxyphenyl)piperazine, 1-(2-chlorophenyl)piperazine, 1-(3-chlorophenyl) piperazine, 1-(4-chlorophenyl)piperazine, 1-(2-methoxyphenyl)piperazine, 1-(3-methoxyphenyl) piperazine, 1-(4-methoxyphenyl)piperazine, 1-(4-methanesulfonamidophenyl)piperazine, 1-(4-cyanophenyl) piperazine, 1-(4-carbamoylphenyl)piperazine, 1-(4-methoxycarbonylphenyl)piperazine, 1-(2-pyridyl) piperazine, 1-(2-pyrimidinyl)piperazine, 1-benzyl piperazine, 1-diphenylmethylpiperazine, 1-cinnamylpiperazine, 1-benzoylpiperazine, 1-(4-benzyloxybenzoyl)piperazine, 1-(4-hydroxybenzoyl) piperazine, 1-(2-furoyl)piperazine, 1-(1,2-benzisoxazol-3-yl)piperazine, 1-(1,2-benzisothiazol-3-yl)piperazine, 4-phenylpiperidine, 4-benzylpiperidine, α, α-bis(4-fluorophenyl)-4-piperidinemethanol, 4-(4-fluorobenzoyl) piperidine, 4-benzoylpiperidine, 4-(4-methoxybenzoyl) piperidine, 4-(4-chlorobenzoyl)piperidine, 3-(4-fluorobenzoyl)piperidine, 4-(6-fluoro-1,2-benzisoxazol-3-yl)piperidine, 4-(6-fluoro-1,2-benzisothiazol-3-yl) piperidine, 4-(6-fluoro-1H-indazol-3-yl)piperidine, 3-benzoylpyrrolidine, 3-(4-fluorobenzoyl)pyrrolidine, 4-(4-fluorophenoxy)piperidine, 4-[(4-fluorophenyl)thio] piperidine, 4-[(4-fluorophenyl)sulfinyl]piperidine, 4-[(4-fluorophenyl)sulfonyl]piperidine, 4-[bis(4-fluorophenyl) methylene]piperidine, 4-(4-fluorobenzoyl)piperidine ethylene acetal, and the like. All these compounds are known or can be easily prepared by known processes or a process similar to the known process.

The compound (II) used as a starting material in the above process can be prepared by various processes. One example of such processes comprises converting a known compound (XX) into a sulfone (XXI) using an oxidizing agent such as m-chloro-perbenzoic acid or sodium tungstate/hydrogen peroxide, followed by the reaction of the compound (XXI) with $R_1X_1H$ or $HX_2-G-X_3H$ in the presence of an acid according to the following reaction scheme.

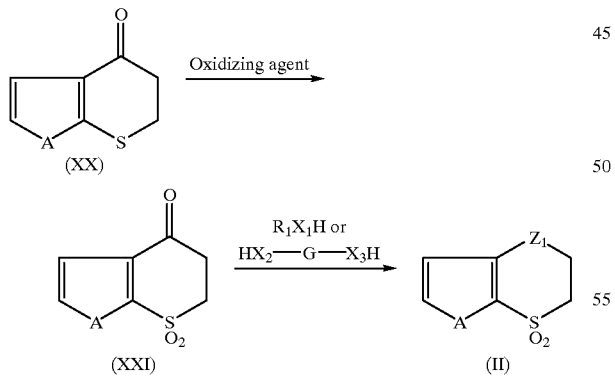

wherein A, G, $R_1$, $X_1$, $X_2$, $X_3$, and $Z_1$ have the same meanings as previously defined.

Process 1B: The compound (Ia) can be prepared by reacting the compound of the formula (II) and a nitrogen-containing compound of the formula (VI) according to the following reaction scheme,

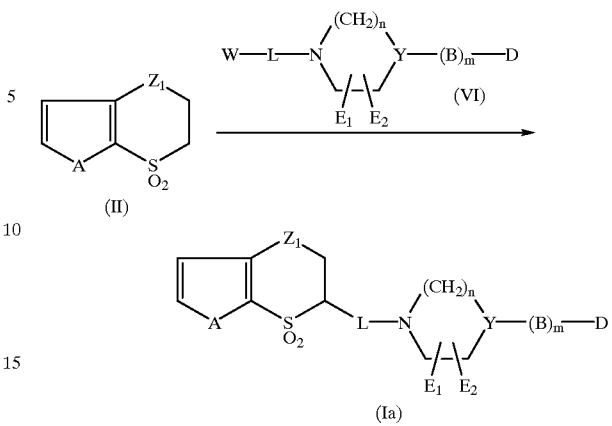

wherein A, B, D, $E_1$, $E_2$, L, W, Y, $Z_1$, m, and n have the same meanings as defined above.

The conversion of the compound (II) into the compound (Ia) is carried out by treating the compound. (II) with an inorganic or organic base and then reacting with the compound (VI). The same reaction conditions as used for the conversion of the compound (II) into the compound (IV) in the above Process 1A applies to this reaction. The compound (VI) can be prepared by reacting the compound (III) and the compound (V) according to the conventional method.

<Processes 2>

Among the thiopyran derivatives (I), the compound (Ib) having the following group for Z in the formula (I) can be prepared by one of the following processes.

Process 2A: The compound (Ib) can be prepared by converting the compound (IV) into the compound (IX) and reacting the compound (IX) and a nitrogen-containing compound of the formula (V) according to the following reaction scheme,

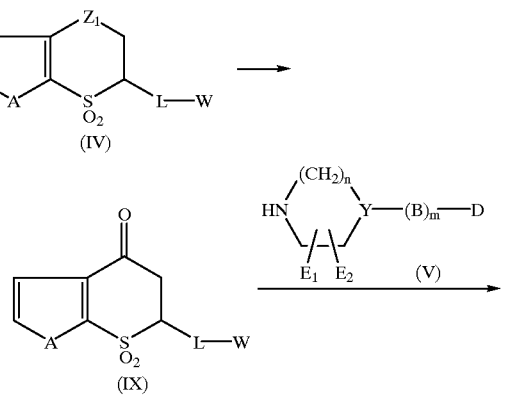

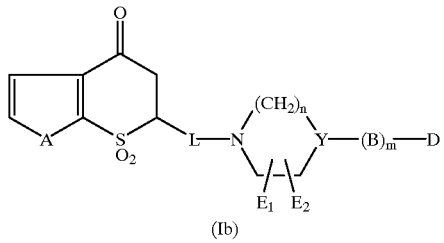

(Ib)

wherein A, B, D, $E_1$, $E_2$, L, W, Y, $Z_1$, m, and n have the same meanings as previously defined.

The conversion of the compound (IV) into the compound (IX) is carried out by a process described, for example, in "Protective Groups in Organic Synthesis" (T. W. Green, published by John Wiley & Sons). For example, the conversion into the target compound (IX) can be carried out by treating with an acid when $X_1$ is an oxygen atom or both $X_2$ and $X_3$ are oxygen atoms or by treating with mercury (II) chloride when $X_1$ is a sulfur atom or both $X_2$ and $X_3$ are sulfur atoms in $Z_1$ of the compound (IV).

The conversion of the compound (IX) into the compound (Ib) can be carried out under the same conditions as in the process for the conversion of the compound (IV) into the compound (Ia) shown in the Process 1A.

Process 2B: The compound (Ib) can be prepared by converting the $Z_1$ portion in the compound (Ia) into a carbonyl group according to the following reaction formula,

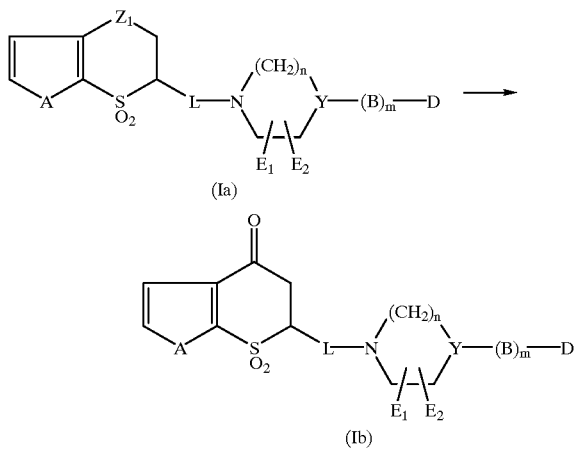

wherein A, B, D, $E_1$, $E_2$, L, Y, $Z_1$, m, and n have the same meanings as previously defined.

The conversion of the compound (Ia) into the compound (Ib) is carried out under the same conditions as in the process for the conversion of the compound (IV) into the compound (IX) in the Process 2A.

<Process 3>

Among the thiopyran derivatives (I), the compound shown by the formula (Id) can be prepared by reacting the compound (Ic) with a thiol compound of the formula (VII) or (VII') accroding to the following reaction scheme,

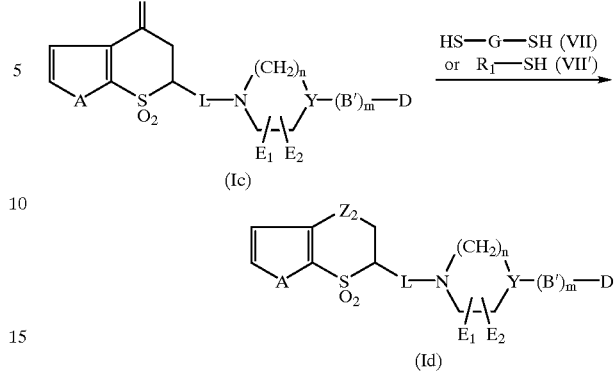

wherein, when Y is CH, B' is an oxygen atom, a sulfur atom, a sulfinyl group, a sulfonyl group, an alkylene group, an alkenylene group, a hydroxymethylene group which may be substituted, a group —$CHR_4$— (wherein $R_4$ is an alkyl group which may be substituted, an aryl group which may be substituted, or an aralkyl group which may be substituted), or a cyclic or acyclic acetal group which may be substituted; when Y is the group C=, B' is the group,

(wherein the double bond is linked to Y and $R_5$ is an alkyl group which may be substituted, an aryl group which may be substituted, or an aralkyl group which may be substituted); and when Y is a nitrogen atom, B' is a carbonyl group, a sulfonyl group, an alkylene group, an alkenylene group, or a group —$CHR_6$— (wherein $R_6$ is an alkyl group which may be substituted, an aryl group which may be substituted, or an aralkyl group which may be substituted); $Z_2$ indicates the group,

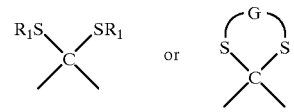

(wherein G and $R_1$ have the same meanings as defined above); and A, D, $E_1$, $E_2$, L, Y, m, and n have the same meanings as previously defined.

The conversion of the compound (Ic) into the compound (Id) is carried out by a process suitably selected from the processes described, for example, in "Protective Groups in Organic Synthesis" (T. W. Green, published by John Wiley & Sons). One example of such processes comprises reacting the compound (Ic) with the compound (VII) or (VII') and boron trifluoride ether complex in chloroform.

<Processes 4>

Among the thiopyran derivatives (I), the compounds (Ig) and (Ie) having the following group,

for Z can be prepared by either the following Process 4A or Process 4B. Process 4A is preferred when the nitrogen-containing compound (V) contains a group which reacts with hydroxylamine or its derivative (VIII), or a salt thereof.

Process 4A: The compound (Ig) can be prepared by reacting a compound of the formula (IX) with hydroxylamine or its derivative (VIII), or a salt thereof, and then reacting the nitrogen-containing compound (V) according to the following reaction

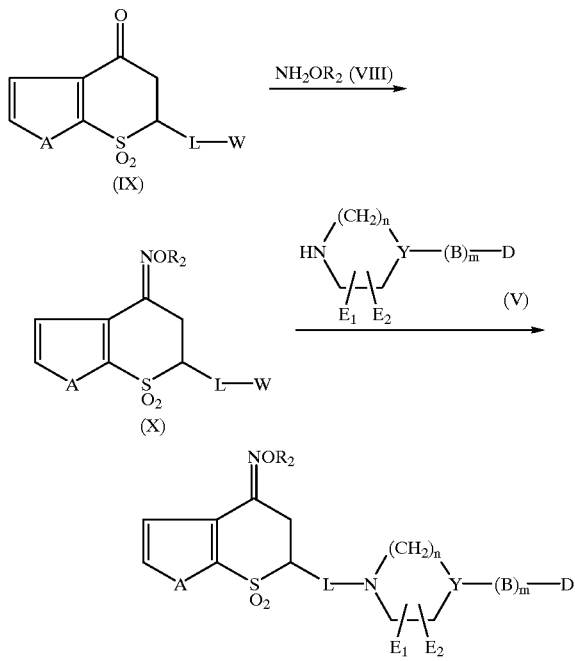

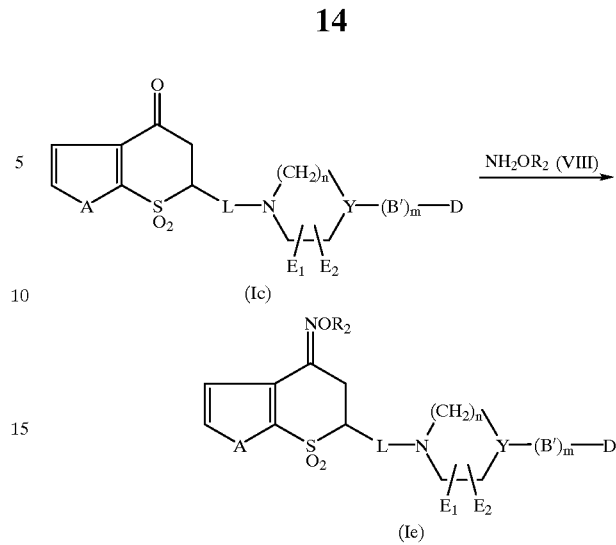

wherein A, B', D, E$_1$, E$_2$, L, R$_2$, Y, m, and n have the same meanings as previously defined.

The same conditions as in the process for the conversion of the compound (IX) into the compound (X) in the Process 4A are applied to the conversion of the compound (Ic) into the compound (Ie).

<Processes 5>

Among the thiopyran derivatives (I), the compounds (Ih) and (If) having the following group,

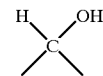

wherein A, B, D, E$_1$, E$_2$, L, R$_2$W, Y, m, and n have the same meanings as previously defined.

The reaction of the compound (IX) with hydroxylamine or its derivative (VIII) can be carried out optionally in the presence of an organic base such as pyridine, triethylamine, collidine, DBU, or sodium acetate, or an inorganic base such as potassium carbonate or sodium hydroxide. In addition, as the hydroxylamine or its derivative (VIII), a salt of an organic or inorganic acid of these compounds may also be used.

If required, this reaction is carried out using a suitable solvent such as methanol, ethanol, propanol, tetrahydrofuran, dimethylformamide, or dimethylsulfoxide, at a temperature from 0° C. to the refluxing temperature, preferably from 0° C. to 100° C.

The conversion of the compound (X) thus obtained into the compound (Ig) is carried out under the same conditions as in the process for the conversion of the compound (IV) into the compound (Ia) in the Process 1A.

Process 4B: The compound (Ie) can be prepared by reacting the compound (Ic) with hydroxylamine or its derivative (VIII), or a salt thereof according to the following reaction scheme, for Z can be prepared by either the following Process 5A or Process 5B. The Process 5A is preferred when the nitrogen-containing compound (V) contains a group which reacts with a reducing agent.

Process 5A: The compound (Ih) can be prepared by reducing a compound of the formula (IX) to produce the compound (XI), and then reacting the nitrogen-containing compound (V) according to the following formula,

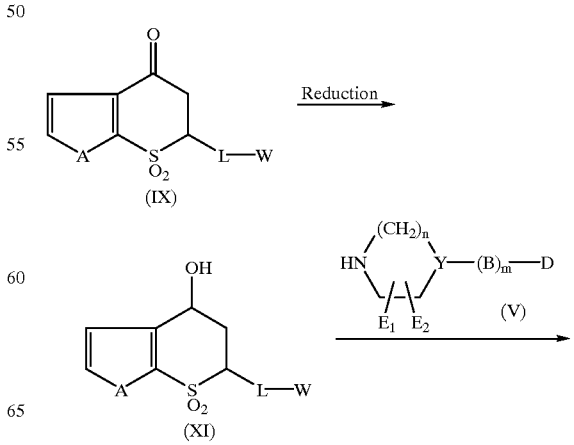

-continued

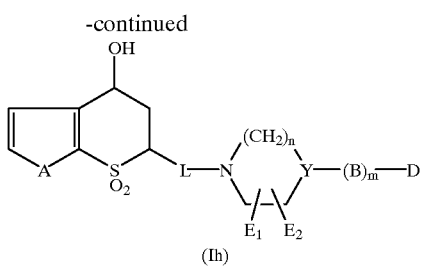

(Ih)

wherein A, B, D, $E_1$, $E_2$, L, W, Y, m, and n have the same meanings as previously defined.

The conversion of the compound (IX) into the compound (XI) can be carried out by treating the compound (IX) with a reducing agent such as sodium borohydride, potassium borohydride or sodium cyanoborohydride in a solvent commonly used at a temperature from −78° C. to the refluxing temperature, preferably from −20° C. to room temperature.

The conversion of the compound (XI) into the compound (Ih) is carried out under the same conditions as in the process for the conversion of the compound (IV) into the compound (Ia) in the Process 1A.

Process 5B: The compound (If) can be prepared by reducing the compound (Ic) according to the following formula,

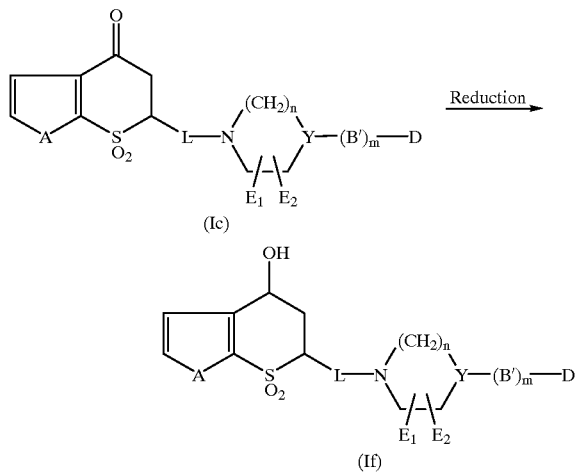

wherein A, B', D, $E_1$, $E_2$, L, Y, m, and n have the same meanings as previously defined.

The same conditions as in the process for the conversion of the compound (IX) into the compound (XI) in the Process 5A can be applied to the conversion of the compound (Ic) into the compound (If).

<Process 6>

Among the thiopyran derivatives (I), the compounds (Ii) having the following group,

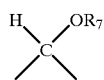

(wherein $R_7$ is an alkyl group which may be substituted or an aralkyl group which may be substituted) for Z can be prepared by reacting a compound of the formula (XI) and a compound of the formula (XII) to produce a compound of the formula (XIII), and reacting this compound with the nitrogen-containing compound (V) according to the following reaction scheme,

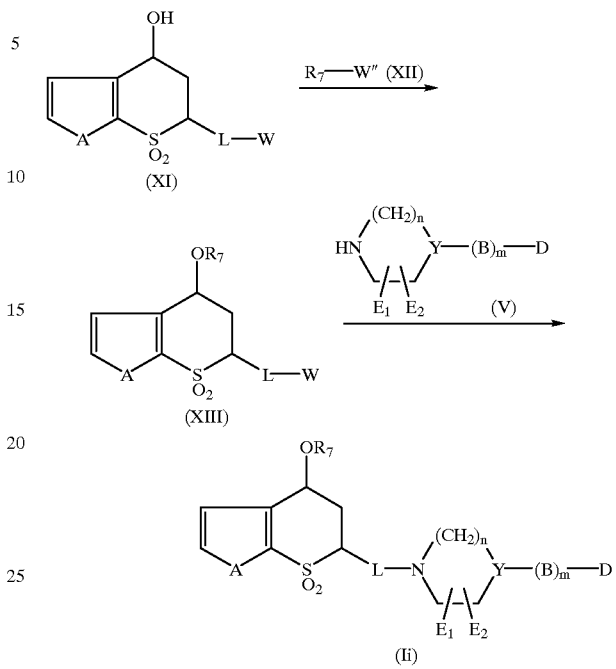

wherein W" indicates a leaving group and A, B, D, $E_1$, $E_2$, L, $R_7$, W, Y, m, and n have the same meanings as previously defined.

The conversion of the compound (XI) into the compound (XIII) can be carried out by treating the compound (XI) with an inorganic or organic base and reacting the compound (XI) with the compound (XII) in the presence of such a base.

The group W" in the compound (XII) is a leaving group typified by a halogen atom such as chlorine or bromine, an alkyl sulfonyloxy group such as methanesulfonyloxy group, or an aryl sulfonyloxy group such as p-toluenesulfonyloxy group.

Given as examples of the inorganic or organic base used in this reaction are sodium hydride, sodium bis(trimethylsilyl) amide, lithium di-isopropylamide, and potassium t-butoxide. As examples of the solvent used in the reaction, tetrahydrofuran, dioxane, dimethylformamide, dimethylsulfoxide, N-methylpyrrolidone, and toluene are given. The reaction is preferably carried out at −78° C. to refluxing temperature.

The same conditions as in the process for the conversion of the compound (IV) into the compound (Ia) in the Process 1A can be applied to the conversion of the compound (XIII) into the compound (Ii).

<Processes 7>

Among the thiopyran derivatives (I), the compounds (Ij) having the following group,

for Z can be prepared by either Process 7A or Process 7B.

Process 7A: The compounds (Ij) can be prepared by converting a compound of the formula (XI) into a compound of the formula (XIV) by dehydration, and reacting this compound with the nitrogen-containing compound (V) according to the following scheme,

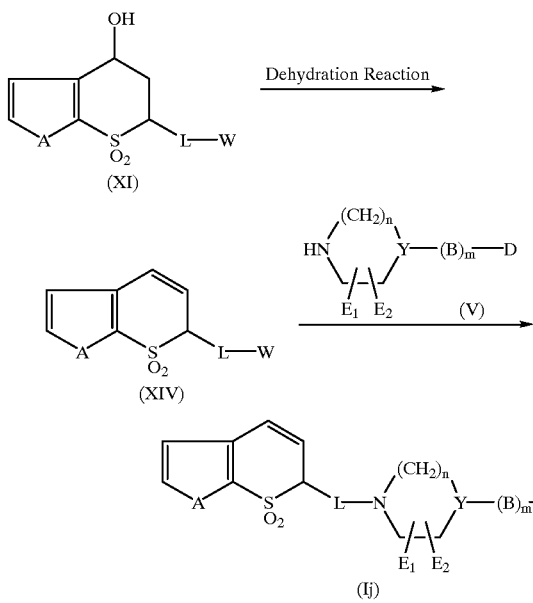

wherein A, B, D, $E_1$, $E_2$, L, W, Y, m, and n have the same meanings as previously defined.

The conversion of the compound (XI) into the compound (XIV) in the above reaction can be carried out by treating the compound (XI) with an acid such as hydrochloric acid, hydrobromic acid, sulfuric acid, or methanesulfonic acid, optionally in the presence of a solvent such as water, methanol, ethanol, or chloroform, or by reacting the compound (XI) with methanesulfonyl chloride or p-toluenesulfonyl chloride and a base such as triethylamine, pyridine, or collidine in a solvent such as dichloromethane, chloroform, or toluene, and treating the resulting compound with said base or silica gel at room temperature to refluxing temperature.

The same conditions as in the process for the conversion of the compound (IV) into the compound (Ia) in the Process 1A can be applied to the conversion of the compound (XIV) into the compound (Ij).

Process 7B: Alternatively, the compounds (Ij) can be prepared by subjecting a compound of the formula (Ih) to a dehydration treatment according to the following scheme,

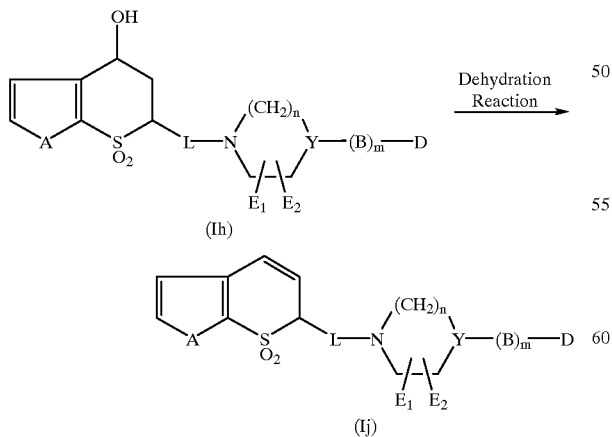

wherein A, B, D, $E_1$, $E_2$, L, Y, m, and n have the same meanings as previously defined.

The same conditions as in the process for the conversion of the compound (XI) into the compound (XIV) in the Process 7A can be applied to the conversion of the compound (Ih) into the compound (Ij).

<Process 8>

Among the thiopyran derivatives (I), the compounds (Ik) having the following group,

for Z can be prepared by reducing a compound of the formula (XIV) into a compound of the formula (XV), and reacting this compound with the nitrogen-containing compound (V) according to the following scheme,

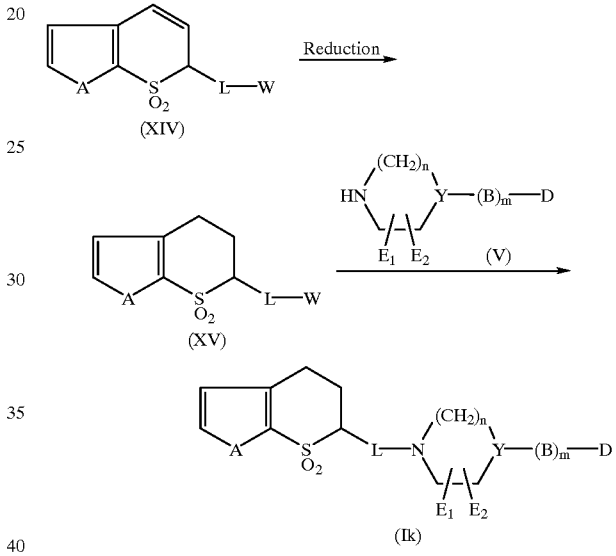

wherein A, B, D, $E_1$, $E_2$, L, W, Y, m, and n have the same meanings as previously defined.

The conversion of the compound (XIV) into the compound (XV) can be carried out by treating the compound (XIV) with hydrogen gas in the presence of a catalyst such as palladium-carbon or platinum in a commonly used solvent at a temperature from −78° C. to refluxing temperature, preferably at room temperature. The same conditions as in the process for the conversion of the compound (IV) into the compound (Ia) in the Process 1A can be applied to the conversion of the compound (XV) into the compound (Ik).

<Process 9>

The thiopyran derivative represented by the following formula (I'),

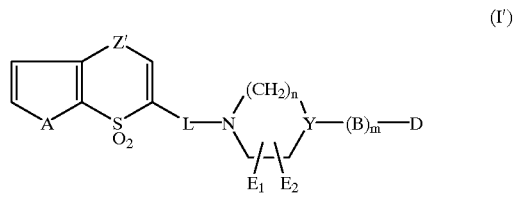

wherein Z' indicates the following group,

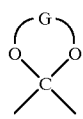

(wherein G has the same meaning as previously defined), and A, B, D, $E_1$, $E_2$, L, Y, m, and n have the same meanings as previously defined, can be prepared by converting a compound of the formula (XVI) into a compound of the formula (XVII), and reacting this compound with the nitrogen-containing compound (V) according to the following scheme,

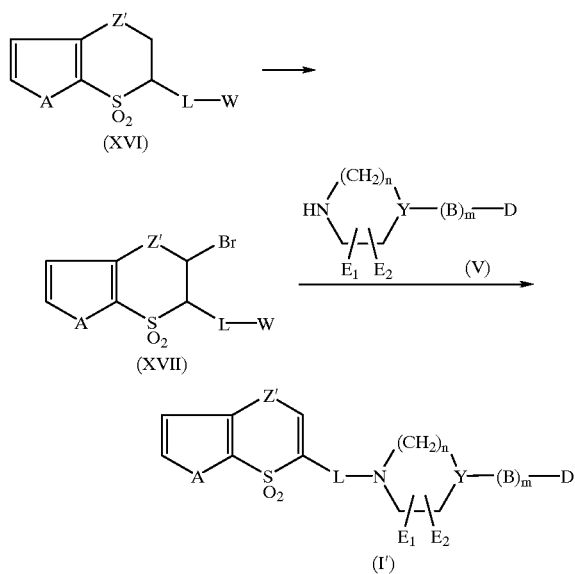

wherein A, B, D, $E_1$, $E_2$, L, W, Y, Z', m, and n have the same meanings as previously defined, In the above reaction, the conversion of the compound (XVI) into the compound (XVII) can be implemented with reference to published literature (B. D. Mookherjee et al., J. Org. Chem., vol. 36, pp 4124–4125 (1971)). The conversion of the compound (XVII) into the compound (I') is carried out under the same conditions as in the process for the conversion of the compound (IV) into the compound (Ia) in the Process 1A.

As required, the compound (I) or (I') of the present invention prepared by the above processes can be reacted with various acids to convert into the salt. The salt can be purified by any suitable means such as recrystallization or column chromatography.

The acid used for converting the thiopyran derivative (I) or (I') into the salt may be an inorganic acid such as hydrochloric acid, nitric acid, sulfuric acid, phosphoric acid, or hydrobromic acid, or an organic acid such as maleic acid, fumaric acid, tartaric acid, lactic acid, citric acid, acetic acid, methanesulfonic acid, p-toluenesulfonic acid, adipic acid, palmitic acid, or tannic acid.

The thiopyran derivatives (I) or (I') include the compounds containing asymmetric centers. It is possible to obtain a pure optical isomer by isolation from racemates by various methods, such as (1) a method of separating using an optically active column, (2) a method comprising converting the racemate into a salt using an optically active acid and separating by recrystallization, (3) a method of separating by an enzymatic reaction, or (4) a method comprising any combination of (1) to (3).

As demonstrated in the test examples hereinafter, the thiopyran derivatives (I) or (I'), or the salts thereof, prepared by the methods described above exhibited a strong serotonin-2 blocking action, and some of them were found to possess both strong serotonin-2 blocking action and $\alpha_1$-blocking action. In addition, these compounds were confirmed to be highly safe as a result of toxicity tests. These compounds therefore are useful as drugs for the treatment of circulatory diseases such as ischemic heart disease, cerebrovascular disturbance, peripheral circulatory disturbance, and hypertension.

When the thiopyran derivatives (I) or (I') of the present invention are used as a drug, an effective amount of these compounds may be administered as is or may be administered after having been formulated in any optional form of drug using known methods.

Peroral drug forms such as tablets, powders, granules, capsules, and syrups, or non-peroral drug forms such as injections or suppositories are given as the type of drug forms which can be used. Any known liquid or solid diluents or carriers conventionally used for drugs can be used for the preparation of the drugs from the thiopyran derivatives (I) or (I') of the present invention.

Given as examples of the diluents or carriers are polyvinyl pyrrolidone, arabic gum, gelatin, sorbit, cyclodextrin, tragacanth, magnesium stearate, talc, polyethylene glycol, polyvinyl alcohol, silica, lactose, crystalline cellulose, sucrose, starch, calcium phosphate, vegetable oils, carboxymethyl cellulose, sodium lauryl sulfate, water, ethanol, glycerin, mannitol, syrup, and the like.

A dose of the compound of the present invention when used as a drug by peroral administration is generally about 0.01 to 1,000 mg/day, although a specific amount varies depending on age, weight, and condition of the patient.

Other features of the invention will become apparent in the course of the following description of the exemplary embodiments which are given for illustration of the invention and are not intended to be limiting thereof.

EXAMPLES

Example 1

Synthesis of 3,4-dihydro-2H-1-benzothiopyran-4-one 1,1-dioxide (Compound 1)

12.94 g (60 mmol) of 80% m-chloroperbenzoic acid was added in portions to a solution of 3.28 g (20 mmol) of thiochroman-4-one in methylene chloride (250 ml) while stirring under cooling with ice. The mixture was stirred at 0° C. for one hour and then at room temperature for 43 hours.

The reaction mixture was filtered, and the filtrate was washed with a 10% aqueous solution of sodium carbonate, 20% aqueous solution of sodium hydrogen sulfite (twice), 10% aqueous solution of sodium carbonate (twice), and saturated brine, dried over anhydrous sodium sulfate, and concentrated under vacuum.

The resultant crude product was recrystallized from ethanol to obtain 3.14 g (yield: 80%) of the title compound.

Example 2

Synthesis of 3,4-dihydro-2H-1-benzothiopyran-4-spiro-2'-(1',3'-dioxorane) 1,1-dioxide (Compound 2)

A mixture of 4.91 g (25 mmol) of the Compound 1, 31.04 g (500 mmol) of ethylene glycol, 951 mg (5 mmol) of p-toluenesulfonic acid mono-hydrate, and 300 ml of toluene was refluxed in a vessel equipped with a Dean & Stark water separator for 88 hours.

The reaction mixture was concentrated under vacuum, and ethyl acetate was added to the residue. The organic layer was washed with saturated aqueous solution of sodium hydrogen carbonate and saturated brine, dried over anhydrous sodium sulfate, and concentrated under vacuum.

The resultant crude product was washed with diethyl ether to obtain 5.39 g (yield: 90%) of the title compound.

Example 3

Synthesis of 2-(3-chloropropyl)-3,4-dihydro-2H-1-benzothiopyran-4-spiro-2'-(1',3'-dioxorane) 1,1-dioxide (Compound 3)

To a solution of 3.84 g (16 mmol) of the Compound 2 in 100 ml of tetrahydrofuran, 48 ml of a 1.0 M tetrahydrofuran solution of sodium bis (trimethylsilyl) amide (48 mmol) was added in portions under stirring and cooling at −78° C. The mixture was stirred at this temperature for 3 hours. Next, a solution of 7.56 g (48 mmol) of 1-bromo-3-chloropropane in 50 ml of tetrahydrofuran was added at −78° C., followed by stirring at this temperature for one hour and at room temperature for 14 hours.

The reaction mixture was concentrated under vacuum, and chloroform was added to the residue. The organic layer was washed with a half-saturated aqueous solution of potassium carbonate and saturated brine, dried over anhydrous sodium sulfate, and concentrated under vacuum. The residue was purified by silica gel column chromatography using silica gel No. 9385™ (manufactured by Merck Co., the same silica gel was used in Examples hereinafter) and a 1:2 ethyl acetate-hexane solution to obtain 2.53 g (yield: 50%) of the title compound.

Example 4

Synthesis of 6-(3-chloropropyl)-5,6-dihydro-4H-thieno[2,3-b]thiopyran-4-spiro-2'-(1',3'-dioxorane) 7,7-dioxide (Compound 4)

The same reaction as that of Example 3 was carried out using 493 mg (2 mmol) of 5,6-dihydro-4H-thieno[2,3-b]thiopyran-4-spiro-2'-(1',3'-dioxorane) 7,7-dioxide, 2 ml of a 1.0 M tetrahydrofuran solution of sodium bis(trimethylsilyl) amide (2 mmol), 1.26 g (8 mmol) of 1-bromo-3-chloropropane, and 20 ml of tetrahydrofuran.

The reaction mixture was concentrated under vacuum, and ethyl acetate was added to the residue. The organic layer was washed with a half-saturated aqueous solution of potassium carbonate and saturated brine, dried over anhydrous sodium sulfate, and concentrated under vacuum. The residue was purified by silica gel column chromatography using a 1:2 ethyl acetate-hexane solution as an eluent to obtain 380 mg (yield: 59%) of the title compound.

Example 5

Synthesis of 2-(3-chloropropyl)-3,4-dihydro-2H-1-benzothiopyran-4-one 1,1-dioxide (Compound 5)

20 ml of 3 N hydrochloric acid solution was added to a solution of 950 mg (3 mmol) of the Compound 3 in 10 ml of ethanol, and the mixture was refluxed for two hours. The reaction mixture was concentrated under reduced pressure. After the addition of 30 ml of 2 N aqueous solution of sodium hydroxide, the residue was extracted with chloroform (three times). The organic layer was washed with water and saturated brine, dried over anhydrous sodium sulfate, and concentrated under vacuum. The residue was purified by silica gel column chromatography (eluent:chloroform) to obtain 818 mg (yield: 100%) of the title compound.

Example 6

Synthesis of 2-(3-chloropropyl)-4-hydroxy-3,4-dihydro-2H-1-benzothiopyran 1,1-dioxide (Compound 6)

200 mg (5.29 mmol) of sodium borohydride was added in portions to a solution of 620 mg (2.27 mmol) of the Compound 5 in 20 ml of ethanol while stirring under cooling with ice. After stirring for 17 hours at room temperature, the reaction mixture was concentrated under vacuum. A 0.1 M phosphate buffer solution (pH 6.0) was added to the residue and the mixture was extracted with chloroform (three times). The organic layer was washed with water and saturated brine, dried over anhydrous sodium sulfate, and concentrated under vacuum. The residue was purified by silica gel column chromatography using a 1:1 ethyl acetate-hexane solution as an eluent to obtain 567 mg (yield: 91%) of the title compound.

Example 7

Synthesis of 3-bromo-2-(3-chloropropyl)-3,4-dihydro-2H-1-benzothiopyran-4-spiro-2'-(1',3'-dioxorane) 1,1-dioxide (Compound 7)

To a solution of 1.58 g (5 mmol) of the Compound 3 in 70 ml of tetrahydrofuran, 5.64 g (15 mmol) of phenyltrimethylammonium tribromide was added in one portion with stirring and cooling with ice. The mixture was stirred for one hour while cooling with ice and then for 65 hours at room temperature. 70 ml of a saturated aqueous solution of sodium hydrogen carbonate was added to the reaction mixture, and the tetrahydrofuran was evaporated at a low temperature under vacuum. The residue was extracted with diethyl ether, and the organic layer was washed with saturated brine, dried over anhydrous sodium sulfate, and concentrated under vacuum. The residue was purified by silica gel column chromatography (eluent: ethyl acetate:hexane= 1:4→1:2) to obtain 1.41 g (yield: 71%) of the title compound.

Example 8

Synthesis of 2-[3-(4-phenylpiperazin-1-yl)propyl]-3,4-dihydro-2H-1-benzothiopyran-4-spiro-2'-(1',3'-dioxorane) 1,1-dioxide (Compound 8)

A suspension containing 317 mg (1 mmol) of the Compound 3, 162 mg (1 mmol) of 1-phenylpiperazine, 168 mg (2 mmol) of sodium hydrogen carbonate, and 300 mg (2 mmol) of sodium iodide in 15 ml of acetonitrile was refluxed for 15 hours. The reaction mixture was concentrated under vacuum. 50 ml of a half saturated aqueous solution of potassium carbonate was added to the residue and the mixture was extracted with chloroform. The organic layer was washed with saturated brine, dried over anhydrous sodium sulfate, and concentrated under vacuum. The residue was purified by silica gel column chromatography using a 2:98 methanol-chloroform solution as an eluent to obtain 400 mg (yield: 90%) of the title compound.

Example 9

Synthesis of 2-[3-(4-phenylpiperidino)propyl]-3,4-dihydro-2H-1-benzothiopyran-4-spiro-2'-(1',3'-dioxorane) 1,1-dioxide (Compound 9)

A suspension containing 317 mg (1 mmol) of the Compound 3, 161 mg (1 mmol) of 4-phenylpiperidine, 168 mg (2 mmol) of sodium hydrogen carbonate, and 300 mg (2 mmol) of sodium iodide in 15 ml of acetonitrile was refluxed for 18 hours. After the post treatment in the same manner as in Example 8, the residue was purified by silica gel column chromatography (eluent: methanol:chloroform=3:97) to obtain 350 mg (yield: 79%) of the title compound.

Example 10

Synthesis of 2-[3-[4-(6-fluoro-1,2-benzisoxazol-3-yl)piperidino]propyl]-3,4-dihydro-2H-1-benzothiopyran-4-spiro-2'-(1',3'-dioxorane) 1,1-dioxide (Compound 10)

A suspension containing 317 mg (1 mmol) of the Compound 3, 220 mg (1 mmol) of 4-(6-fluoro-1,2-benzisoxazol-3-yl)piperidine, 168 mg (2 mmol) of sodium hydrogen carbonate, and 300 mg (2 mmol) of sodium iodide in 15 ml of acetonitrile was refluxed for 17 hours. After the post treatment in the same manner as in Example 8, the residue was purified by silica gel column chromatography (eluent: methanol:chloroform=1:99) to obtain 465 mg (yield: 93%) of the title compound.

Example 11

Synthesis of 2-[3-[4-(2-pyrimidinyl)piperazin-1-yl]propyl]-3,4-dihydro-2H-1-benzothiopyran-4-spiro-2'-(1',3'-dioxorane) 1,1-dioxide (Compound 11)

A suspension containing 317 mg (1 mmol) of the Compound 3, 237 mg (1 mmol) of 1-(2-pyrimidyl)piperazine dihydrochloride, 504 mg (6 mmol) of sodium hydrogen carbonate, and 300 mg (2 mmol) of sodium iodide in 15 ml of acetonitrile was refluxed for 17 hours. The reaction mixture was post treated and purified in the same manner as in Example 9 to obtain 404 mg (yield:91%) of the title compound.

Example 12

Synthesis of 2-[3-[4-(4-fluorobenzoyl)piperidino]propyl]-3,4-dihydro-2H-1-benzothiopyran-4-spiro-2'-(1',3'-dioxorane) 1,1-dioxide (Compound 12)

A suspension containing 317 mg (1 mmol) of the Compound 3, 244 mg (1 mmol) of 4-(4-f luorobenzoyl)piperidine hydrochloride, 336 mg (4 mmol) of sodium hydrogen carbonate, and 300 mg (2 mmol) of sodium iodide in 15 ml of acetonitrile was refluxed for 15 hours. The reaction mixture was post treated and purified in the same manner as in Example 9 to obtain 426 mg (yield:87%) of the title compound. aaa Example 13

Synthesis of 2-[3-[4-(4-hydroxyphenyl)piperazin-1-yl]propyl]-3,4-dihydro-2H-1-benzothiopyran-4-spiro-2'-(1',3'-dioxorane) 1,1-dioxide (Compound 13)

A suspension containing 95 mg (0.30 mmol) of the Compound 3, 86 mg (0.33 mmol) of 1-(4-hydroxyphenyl)piperazine hydrobromide, 112 mg (1.33 mmol) of sodium hydrogen carbonate, and 100 mg (0.66 mmol) of sodium iodide in 10 ml of acetonitrile was refluxed for 18 hours. The reaction mixture was filtered and the filtrate was concentrated under vacuum. The residue was purified by silica gel column chromatography (eluent:methanol:chloroform=3:97) to obtain 84 mg (yield: 61%) of the title compound.

Example 14

Synthesis of 6-[3-[4-(4-hydroxyphenyl)piperazin-1-yl]propyl]-5,6-dihydro-4H-thieno[2,3-6]thiopyran-4-spiro-2'-(1',3'-dioxorane) 7,7-dioxide (Compound 14)

A suspension containing 226 mg (0.7 mmol) of the Compound 4, 181 mg (0.7 mmol) of 1-(4-hydroxyphenyl)piperazine hydrobromide, 235 mg (2.8 mmol) of sodium hydrogen carbonate, and 210 mg (1.4 mmol) of sodium iodide in 15 ml of acetonitrile was refluxed for 16 hours. The reaction mixture was treated and purified in the same manner as in Example 13 to obtain 223 mg (yield: 69%) of the title compound.

Example 15

Synthesis of 6-[3-(4-phenylpiperazin-1-yl)propyl]-5,6-dihydro-4H-thieno[2,3-b]thiopyran-4-spiro-2'-(1',3'-dioxorane) 7,7-dioxide (Compound 15)

A suspension containing 323 mg (1 mmol) of the Compound 4, 162 mg (1 mmol) of 1-phenylpiperazine, 168 mg (2 mmol) of sodium hydrogen carbonate, and 300 mg (2 mmol) of sodium iodide in 15 ml of acetonitrile was refluxed for 16 hours. After the post treatment in the same manner as in Example 8, the residue was separated by silica gel column chromatography (eluent:methanol:chloroform=2:98). The crude compound obtained was recrystallized from ethyl acetate-hexane to obtain 216 mg (yield: 48%) of the title compound.

Example 16

Synthesis of 2-[3-[4-(4-fluorophenyl)piperazin-1-yl]propyl]-3,4-dihydro-2H-1-benzothiopyran-4-spiro-2'-(1',3'-dioxorane) 1,1-dioxide (Compound 16)

To a solution of 30.0 g (125 mmol) of the Compound 2 in 400 ml of tetrahydrofuran, 125 ml of a 1.0 M tetrahydrofuran solution of sodium bis(trimethylsilyl)amide (125 mmol) was added in dropwise under stirring and cooling at −78° C. The mixture was stirred at this temperature for 3.5 hours. Next, a solution of 32.1 g (125 mmol) of 1-(3-chloropropyl)-4-(4-fluorophenyl)piperazine in 100 ml of tetrahydrofuran was slowly added dropwise at −78° C., followed by stirring at this temperature for 30 minutes and at room temperature for 18 hours.

The reaction mixture was concentrated under vacuum. 500 ml of a half-saturated aqueous solution of potassium carbonate was added to the residue, and the mixture was extracted with ethyl acetate. The ethyl acetate layer was washed with water (twice) and saturated brine, dried over anhydrous sodium sulfate, and concentrated under vacuum. The crude product was washed with diethyl ether, followed by recrystallization from ethyl acetate-hexane to obtain 38.51 g (yield: 67%) of the title compound.

Example 17

Synthesis of 2-[2-[4-(4-fluorophenyl)piperazin-1-yl]ethyl]-3,4-dihydro-2H-1-benzothiopyran-4-spiro-2'-(1',3'-dioxorane) 1,1-dioxide (Compound 17)

The same reaction and the post treatment as those of Example 16 were carried out using 240 mg (1 mmol) of the Compound 2, 1 ml of a 1.0 M tetrahydrofuran solution of sodium bis(trimethylsilyl)amide (1 mmol), 243 mg (1 mmol) of 1-(2-chloroethyl)-4-(4-fluorophenyl)piperazine, and 10 ml of tetrahydrofuran. The residue obtained was purified by silica gel column chromatography (eluent:ethyl acetate:hexane=1:1) to obtain 108 mg (yield: 24%) of the title compound.

Example 18

Synthesis of 6-[3-[4-(4-fluorophenyl)piperazin-1-yl]propyl]5,6-dihydro-4H-thieno[2,3-b]thiopyran-4-spiro-2'-(1',3'-dioxorane) 7,7-dioxide (Compound 18)

The same reaction and the post treatment as those of Example 16 were carried out using 2.46 g (10 mmol) of 5,6-dihydro-4H-thieno[2,3-b]thiopyran-4-spiro-2'-(1',3'-dioxorane) 7,7-dioxide, 12 ml of a 1.0 M tetrahydrofuran solution of sodium bis(trimethylsilyl)amide (12 mmol), 3.08 g (12 mmol) of 1-( 3-chloropropyl)-4-(4-fluorophenyl)piperazine, and 100 ml of tetrahydrofuran. The residue obtained was purified by silica gel column chromatography (eluent:ethyl acetate) to obtain 2.51 g (yield: 54%) of the title compound.

Example 19

Synthesis of 2-[3-[4-(4-fluorophenyl)piperazin-1-yl]propyl]-3,4-dihydro-2H-1-benzothiopyran-4-one 1,1-dioxide (Compound 19)

10 ml of 3 N hydrochloric acid was added to a solution of 461 mg (1 mmol) of the Compound 16 in 5 ml of methanol, and the mixture was refluxed for one hour. The reaction mixture was concentrated under vacuum. 50 ml of a half-saturated aqueous solution of potassium carbonate was added to the residue and the mixture was extracted with chloroform (twice). The organic layer was washed with saturated brine, dried over anhydrous sodium sulfate, and concentrated under vacuum to obtain 415 mg (yield: 100%) of the title compound.

Example 20

Synthesis of 6-[3-[4-(4-fluorophenyl)piperazin-1-yl]propyl]-5,6-dihydro-4H-thieno[2,3-b]thiopyran-4-one 7,7-dioxide (Compound 20)

40 ml of 2 N hydrochloric acid was added to a suspension of 1.40 g (3 mmol) of the Compound 18 in 20 ml of methanol, and the mixture was refluxed for 30 minutes. The reaction mixture was concentrated under vacuum. 100 ml of 1 N aqueous solution of sodium hydroxide was added to the residue and the mixture was extracted with chloroform (twice). The organic layer was washed with saturated brine, dried over anhydrous sodium sulfate, and concentrated under vacuum. The residue obtained was purified by silica gel column chromatography (eluent:ethyl acetate:hexane=1:1) to obtain 1.22 g (yield: 96%) of the title compound.

Example 21

Synthesis of 2-[3-[4-(4-fluorophenyl)piperazin-1-yl]propyl]-3,4-dihydro-2H-1-benzothiopyran-4-spiro-2'-(1',3'-dithiorane) 1,1-dioxide (Compound 21)

67 µl (0.8 mmol) of 1,2-ethanedithiol and 10 ml of acetic acid were added to a solution of 167 mg (0.4 mmol) of the Compound 19 in 10 ml of methylene chloride. 98 µl (0.8 mmol) of borontrifluoride-ether complex was added in portions while stirring under cooling with ice, and the mixture was stirred for 96 hours at room temperature. After neutralization of the resulting reaction mixture with 1 N sodium hydroxide aqueous solution, a half-saturated aqueous solution of potassium carbonate was added and the mixture was extracted with methylene chloride. The organic layer was washed with saturated brine, dried over anhydrous sodium sulfate, and concentrated under vacuum. The residue was purified by silica gel column chromatography (eluent:methanol:chloroform=1:99) to obtain 122 mg (yield: 62%) of the title compound.

Example 22

Synthesis of 2-[3-[4-(4-fluorophenyl)piperazin-1-yl]propyl]-4-hydroxyimino-3,4-dihydro-2H-1-benzothiopyran 1,1-dioxide (Compound 22)

A solution of 417 mg (1 mmol) of the Compound 19, 139 mg (2 mmol) of hydroxylamine hydrochloride, and 164 mg (2 mmol) of sodium acetate in 15 ml of methanol was refluxed for 17 hours. After the post treatment in the same manner as in Example 8, the residue was recrystallized from acetonitrile to obtain 381 mg (yield: 88%) of the title compound.

Example 23

Synthesis of 2-[3-[4-(4-fluorophenyl)piperazin-1-yl]propyl]-4-hydroxy-3,4-dihydro-2H-1-benzothiopyran 1,1-dioxide (Compound 23)

340 mg (9 mmol) of sodium borohydride was added to a suspension of 375 mg (0.9 mmol) of the Compound 19 in 15 ml of methanol while stirring under cooling with ice. After stirring for two hours at room temperature, 15 ml of water was added and the mixture was stirred for one hour at room temperature and concentrated under vacuum. Ethyl acetate was added to the residue and the organic layer was washed with water and saturated brine, dried over anhydrous sodium sulfate, and concentrated under vacuum. The crude product was purified by recrystallizing from ethanol to obtain 230 mg (yield: 61%) of the title compound.

Example 24

Synthesis of 2-[3-[4-(4-fluorophenyl)piperazin-1-yl]propyl]-2H-1-benzothiopyran 1,1-dioxide (Compound 24)

A suspension of 41.9 mg (0.1 mmol) of the Compound 23 in 10 ml of 3 N hydrochloric acid aqueous solution was refluxed for 24 hours. The reaction mixture was cooled with ice, adjusted to pH 10 with a 5 N aqueous solution of sodium hydroxide, and extracted with ethyl acetate. The organic layer was washed with saturated brine, dried over anhydrous sodium sulfate, and concentrated under vacuum. The residue obtained was purified by silica gel column chromatography (eluent:methanol:chloroform=1:99) to obtain 24 mg (yield: 60%) of the title compound.

Example 25

Synthesis of 2-[3-[4-(4-fluorophenyl)piperazin-1-yl]propyl]-4H-1-benzothiopyran-4-spiro-2'-(1',3'-dioxorane) 1,1-dioxide (Compound 25)

A suspension containing 791 mg (2 mmol) of the Compound 7, 360 mg (2 mmol) of 1-(4-fluorophenyl)piperazine, 672 mg (8 mmol) of sodium hydrogen carbonate, and 600 mg (4 mmol) of sodium iodide in 30 ml of acetonitrile was refluxed for 15 hours. The reaction mixture was treated in the same manner as in Example 3 and the residue was purified by silica gel column chromatography (eluent:ethyl acetate:hexane=2:1) to obtain 677 mg (yield: 74%) of the title compound.

Example 26

Separation of optical isomers of 6-[3-[4-(4-fluorophenyl) piperazin-1-yl]propyl]-5,6-dihydro-4H-thieno [2,3-b]thiopyran-4-spiro-2'-(1',3'-dioxorane) 7,7-dioxide (Compound 18) by an optically active column (Compounds 26 and 27)

80 µl of a solution of the Compound 18 in methanol (3.3 mg/ml) was charged into a HPLC column (CHIRALCEL OD-H™, 4.6 φ×250 mm, manufactured by Daicel Chemical Industries, Ltd.) and eluted under the conditions of a column temperature of 40° C.; a mobile phase of a 40:5:30 mixture of n-hexane, ethanol, and methanol; a flow rate of 0.7 ml/min; and detection at 240 nm, to collect eluted fractions. This elution was repeated 20 times and the eluted liquid was concentrated under vacuum to obtain the following optically pure isomers, at a yield of 1.1 mg and 0.96 mg, respectively.
Compound 26: From a first fraction (elution time=9 minutes)
  Characteristics: Colorless needles
  Specific rotatory power: $[\alpha]_D^{31}$ −30.9° (c=0.99, CHCl$_3$)
  Melting point: 164.5–166.0° C.
Compound 27: From a second fraction (elution time=13 minutes)
  Characteristics: Colorless flakes
  Specific rotatory power: $[\alpha]_D^{31}$ +32.4° (c=1.01, CHCl$_3$)
  Melting point: 164.5–166.0° C.

Example 27

Separation of optical isomers of 2-[3-[4-(4-fluorophenyl)-piperazin-1-yl]propyl]-3,4-dihydro-2H-1-benzothiopyran-4-spiro-2'-(1',3'-dioxorane) 1,1-dioxide (Compound 16) by an optically active column (Compounds 28 and 29)

The Compound 16 was separated in the same manner as in Example 26 by a HPLC column (CHIRALPAK AD™, 4.6 φ×250 mm, manufactured by Daicel Chemical Industries, Ltd.; a column temperature of 40° C.; a mobile phase of a 50:6:44 mixture of n-hexane, ethanol, and methanol; a flow rate of 0.4 ml/min; and detection at 240 nm).
Compound 28: From a first fraction (elution time=19 minutes)
  Characteristics: Colorless platy crystals
  Specific rotatory power: $[\alpha]_D^{32}$ −34.6 (c=0.99, CHCl$_3$)
  Melting point: 175.0–176.0° C.
Compound 29: From a second fraction (elution time=23 minutes)
  Characteristics: Colorless platy crystals
  Specific rotatory power: $[\alpha]_D^{32}$ +35.4° (c=0.99, CHCl$_3$)
  Melting point: 175.0–176.0° C.

Example 28

Separation of optical isomers of 6-[3-[4-(4-fluorophenyl)-piperazin-1-yl]propyl)-5,6-dihydro-4H-thieno[2,3-b]thiopyran-4-spiro-2'-(1',3'-dioxorane) 7,7-dioxide (Compound 18) by resolution with an optically active acid (Compounds 26' and 27')

933 mg (2 mmol) of the Compound 18 and 300 mg (2 mmol) of L-(+)-tartaric acid were added to methanol in this order to dissolve with heating. The reaction mixture was concentrated under reduced pressure and crystallized. The crude crystals were recrystallized three times from methanol to obtain 352 mg of Compound 26'. The mother liquor obtained during the recrystallization was neutralized and processed in the same manner with D-(−)-tartaric acid to obtain 300 mg of Compound 27'.

The analysis of these compounds by HPLC under the same conditions as in Example 26 confirmed that the Compound 26' is L-(+)-tartaric acid salt of the Compound 26 and the Compound 27' is D-(−)-tartaric acid salt of the Compound 27.
Compound 26':
  Characteristics: Colorless powdery crystals (Recrystallized from methanol)
  Melting point: 139.5–142.5° C.
Compound 27':
  Characteristics: Colorless powdery crystals (Recrystallized from methanol)
  Melting point: 139.0–142.5° C.

Example 29

The following compounds can be obtained by reacting any one of the compounds of the formula (XVIII) or (XVII), as a thiopyran derivative, and 1-phenylpiperazine, 1-(2-fluorophenyl)-piperazine, 1-(4-fluorophenyl)piperazine, 1-(4-hydroxyphenyl)piperazine, 1-(3-methoxyphenyl) piperazine, 1-(2-pyridyl)piperazine, or 4-(4-fluorobenzoyl) piperidine, as a piperazine or piperidine derivative.

(1) 2-[3-[4-(2-Fluorophenyl)piperazin-1-yl]propyl]-3,4-dihydro-2H-1-benzothiopyran-4-spiro-2'-(1',3'-dioxorane) 1,1-dioxide
(2) 2-[4-[4-(4-Fluorophenyl)piperazin-1-yl]butyl]-3,4-dihydro-2H-1-benzothiopyran-4-spiro-2'-(1',3'-dioxorane) 1,1-dioxide
(3) 2-[3-[4-(3-Methoxyphenyl)piperazin-1-yl]propyl]-3,4-dihydro-2H-1-benzothiopyran-4-spiro-2'-(1',3,-dioxorane) 1,1-dioxide
(4) 2-[3-[4-(2-Pyridyl)piperazin-1-yl]propyl]-3,4-dihydro-2H-1-benzothiopyran-4-spiro-2'-(1',3'-dioxorane) 1,1-dioxide
(5) 2-[3-[4-(4-Hydroxyphenyl)piperazin-1-yl]propyl]-3,4-dihydro-2H-1-benzothiopyran-4-spiro-2'-(1',3'-dithiorane) 1,1-dioxide
(6) 2-(3-[4-(4-Fluorobenzoyl)piperidino]propyl]-3,4-dihydro-2H-1-benzothiopyran-4-spiro-2'-(1',3'-dithiorane) 1,1-dioxide
(7) 2-[3-[4-(2-Fluorophenyl)piperazin-1-yl]propyl]-3,4-dihydro-2H-1-benzothiopyran-4-spiro-2'-(1',3'-dithiorane) 1,1-dioxide
(8) 2-[2-[4-(4-Fluorophenyl)piperazin-1-yl]ethyl]-3,4-dihydro-2H-1-benzothiopyran-4-spiro-2'-(1',3'-dithiorane) 1,1-dioxide
(9) 2-[4-[4-(4-Fluorophenyl)piperazin-1-yl]butyl]-3,4-dihydro-2H-1-benzothiopyran-4-spiro-2'-(1',3'-dithiorane) 1,1-dioxide
(10) 2-[3-[4-(2-Pyridyl)piperazin-1-yl]propyl]-3,4-dihydro-2H-1-benzothiopyran-4-spiro-2'-(1',3'-dithiorane) 1,1-dioxide
(11) 2-[3-[4-(4-Fluorophenyl)piperazin-1-yl]propyl]-4,4-dimethoxy-3,4-dihydro-2H-1-benzothiopyran 1,1-dioxide
(12) 2-[3-[4-(4-Fluorobenzoyl)piperidino]propyl]-4,4-dimethoxy-3,4-dihydro-2H-1-benzothiopyran 1,1-dioxide
(13) 2-[3-[4-(2-Fluorophenyl)piperazin-1-yl]propyl]-4,4-dimethoxy-3, 4-dihydro-2H-1-benzothiopyran 1,1-dioxide

(14) 2-[2-[4-(4-Fluorophenyl)piperazin-1-yl]ethyl]-4,4-dimethoxy-3,4-dihydro-2H-1-benzothiopyran 1,1-dioxide
(15) 2-[4-[4-(4-Fluorophenyl)piperazin-1-yl]butyl]-4,4-dimethoxy-3,4-dihydro-2H-1-benzothiopyran 1,1-dioxide
(16) 4,4-Dimethoxy-2-[3-[4-(2-pyridiyl)piperazin-1-yl]propyl]-3,4-dihydro-2H-1-benzothiopyran 1,1-dioxide
(17) 2-[3-[4-(4-Fluorophenyl)piperazin-1-yl]propyl]-3,4-dihydro-2H-1-benzothiopyran-4-spiro-2'-(1',3'-dioxane) 1,1-dioxide
(18) 2-[3-[4-(4-Fluorobenzoyl)piperidino]propyl]-3,4-dihydro-2H-1-benzothiopyran-4-spiro-2'-(1',3'-dioxane) 1,1-dioxide
(19) 2-[3-[4-(2-Fluorophenyl)piperazin-1-yl]propyl]-3,4-dihydro-2H-1-benzothiopyran-4-spiro-2'-(1',3'-dioxane) 1,1-dioxide
(20) 2-[2-[4-(4-Fluorophenyl)piperazin-1-yl]ethyl]-3,4-dihydro-2H-1-benzothiopyran-4-spiro-2'-(1',3'-dioxane) 1,1-dioxide
(21) 2-[4-[4-(4-Fluorophenyl)piperazin-1-yl]butyl]-3,4-dihydro-2H-1-benzothiopyran-4-spiro-2'-(1',3'-dioxane) 1,1-dioxide
(22) 2-[3-[4-(2-Pyridyl)piperazin-1-yl]propyl]-3,4-dihydro-2H-1-benzothiopyran-4-spiro-2'-(1',3'-dioxane) 1,1-dioxide
(23) 2-[3-[4-(4-Fluorophenyl)piperazin-1-yl]propyl]-3,4-dihydro-2H-1-benzothiopyran-4-spiro-2'-(1',3'-dithiane) 1,1-dioxide
(24) 2-[3-[4-(4-Hydroxyphenyl)piperazin-1-yl]propyl]-3,4-dihydro-2H-1-benzothiopyran-4-spiro-2'-(1',3'-dithiane) 1,1-dioxide
(25) 2-[3-[4-(4-Fluorobenzoyl)piperidino]propyl]-3,4-dihydro-2H-1-benzothiopyran-4-spiro-2'-(1',3'-dithiane) 1,1-dioxide
(26) 4,4-Bis(ethylthio)-2-[3-[4-(4-fluorophenyl)piperazin-1-yl]propyl]-3,4-dihydro-2H-1-benzothiopyran 1,1-dioxide
(27) 2-[3-[4-(4-Hydroxyphenyl)piperazin-1-yl]propyl]-3,4-dihydro-2H-1-benzothiopyran-4-one 1,1-dioxide
(28) 2-[3-[4-(4-Fluorobenzoyl)piperidino]propyl]-3,4-dihydro-2H-1-benzothiopyran-4-one 1,1-dioxide
(29) 4-Hydroxyimino-2-[3-[4-(4-hydroxyphenyl)piperazin-1-yl]propyl]-3,4-dihydro-2H-1-benzothiopyran 1,1-dioxide
(30) 2-[3-[4-(4-Fluorobenzoyl)piperidino]propyl]-4-hydroxyimino-3,4-dihydro-2H-1-benzothiopyran 1,1-dioxide
(31) 4-Hydroxy-2-[3-[4-(4-hydroxyphenyl)piperazin-1-yl]propyl]-3,4-dihydro-2H-1-benzothiopyran 1,1-dioxide
(32) 2-[3-[4-(4-Fluorobenzoyl)piperidino]propyl]-4-hydroxy-3,4-dihydro-2H-1-benzothiopyran 1,1-dioxide
(33) 2-[3-[4-(2-Fluorophenyl)piperazin-1-yl]propyl]-4-hydroxy-3,4-dihydro-2H-1-benzothiopyran 1,1-dioxide
(34) 2-[2-[4-(4-Fluorophenyl)piperazin-1-yl]ethyl]-4-hydroxy-3,4-dihydro-2H-1-benzothiopyran 1,1-dioxide
(35) 2-[4-[4-(4-Fluorophenyl)piperazin-1-yl]butyl]-4-hydroxy-3,4-dihydro-2H-1-benzothiopyran 1,1-dioxide
(36) 4-Hydoxy-2-[3-[4-(2-pyridyl)piperazin-1-yl]propyl]-3,4-dihydro-2H-1-benzothiopyran 1,1-dioxide
(37) 2-[3-[4-(4-Fluorophenyl)piperazin-1-yl]propyl]-4-methoxy-3,4-dihydro-2H-1-benzothiopyran 1,1-dioxide
(38) 2-[3-[4-(4-Hydroxyphenyl)piperazin-1-yl]propyl]-4-methoxy-3,4-dihydro-2H-1-benzothiopyran 1,1-dioxide
(39) 2-[3-[4-(4-Fluorobenzoyl)piperidino]propyl]-4-methoxy-3,4-dihydro-2H-1-benzothiopyran 1,1-dioxide
(40) 2-[3-[4-(2-Fluorophenyl)piperazin-1-yl]propyl]-4-methoxy-3,4-dihydro-2H-1-benzothiopyran 1,1-dioxide
(41) 4-Ethoxy-2-[3-[4-(4-fluorophenyl)piperazin-1-yl]propyl]-3,4-dihydro-2H-1-benzothiopyran 1,1-dioxide
(42) 4-Benzyloxy-2-[3-[4-(4-fluorophenyl)piperazin-1-yl]propyl]-3,4-dihydro-2H-1-benzothiopyran 1,1-dioxide
(43) 4-Benzyloxy-2-[3-[4-(4-hydroxyphenyl)piperazin-1-yl]propyl]-3,4-dihydro-2H-1-benzothiopyran 1,1-dioxide
(44) 4-Benzyloxy-2-[3-[4-(4-fluorobenzoyl)piperidino]propyl]-3,4-dihydro-2H-1-benzothiopyran 1,1-dioxide
(45) 2-[3-[4-(4-Hydroxyphenyl)piperazin-1-yl]propyl]-2H-1-benzothiopyran 1,1-dioxide
(46) 2-[3-[4-(4-Fluorobenzoyl)piperidino]propyl]-2H-1-benzothiopyran 1,1-dioxide
(47) 2-[3-[4-(4-Fluorophenyl)piperazin-1-yl]propyl]-3,4-dihydro-2H-1-benzothiopyran 1,1-dioxide
(48) 2-[3-[4-(4-Hydroxypenyl)piperazin-1-yl]propyl]-3,4-dihydro-2H-1-benzothiopyran 1,1-dioxide
(49) 2-[3-[4-(4-Fluorobenzoyl)piperidino]propyl]-3,4-dihydro-2H-1-benzothiopyran 1,1-dioxide
(50) 6-[3-[4-(4-Fluorobenzoyl)piperidino]propyl]-5,6-dihydro-4H-thieno[2,3-b]thiopyran-4-spiro-2'-(1',3'-dioxorane) 7,7-dioxide
(51) 6-[3-[4-(2-Fluorophenyl)piperazin-a-yl]propyl]-5,6-dihydro-4H-thieno[2,3-b]thiopyran-4-spiro-2'-(1',3'-dioxorane) 7,7-dioxide
(52) 6-[2-[4-(4-Fluorophenyl)piperazin-1-yl]ethyl]-5,6-dihydro-4H-thieno[2,3-b]thiopyran-4-spiro-2'-(1',3'-dioxorane) 7,7-dioxide
(53) 6-[4-[4-(4-Fluorophenyl)piperazin-1-yl]butyl]-5,6-dihydro-4H-thieno[2,3-b]thiopyran-4-spiro-2'-(1',3'-dioxorane) 7,7-dioxide
(54) 6-[3-[4-(3-Methoxyphenyl)piperazin-1-yl]propyl]-5,6-dihydro-4H-thieno[2,3-b]thiopyran-4-spiro-2'-(1',3'-dioxorane) 7,7-dioxide
(55) 6-[3-[4-(2-Pyridyl)piperazin-1-yl]propyl]-5,6-dihydro-4H-thieno[2,3-b]thiopyran-4-spiro-2'-(1',3'-dioxorane) 7,7-dioxide
(56) 6-[3-[4-(4-Fluorophenyl)piperazin-1-yl]propyl]-5,6-dihydro-4H-thieno[2,3-b]thiopyran-4-spiro-2'-(1',3'-dithiorane) 7,7-dioxide
(57) 6-[3-[4-(4-Hyroxyphenyl)piperazin-1-yl]propyl]-5,6-dihydro-4H-thieno[2,3-b]thiopyran-4-spiro-2'-(1',3'-dithiorane) 7,7-dioxide
(58) 6-[3-[4-(4-Fluorobenzoyl)piperidino]propyl]-5,6-dihydro-4H-thieno[2,3-b]thiopyran-4-spiro-2'-(1',3'-dithiorane) 7,7-dioxide
(59) 6-[3-[4-(2-Fluorophenyl)piperazin-1-yl]propyl]-5,6-dihydro-4H-thieno[2,3-b]thiopyran-4-spiro-2'-(1',3'-dithiorane) 7,7-dioxide
(60) 6-[2-[4-(4-Fluorophenyl)piperazin-1-yl]ethyl]-5,6-dihydro-4H-thieno[2,3-b]thiopyran-4-spiro-2'-(1',3'-dithiorane) 7,7-dioxide
(61) 6-[4-[4-(4-Fluorophenyl)piperazin-1-yl]butyl]-5,6-dihydro-4H-thieno[2,3-b]thiopyran-4-spiro-2'-(1',3'-dithiorane) 7,7-dioxide
(62) 6-[3-[4-(2-Pyridyl)piperazin-1-yl]propyl]-5,6-dihydro-4H-thieno[2,3-b]thiopyran-4-spiro-2'-(1',3'-dithiorane) 7,7-dioxide
(63) 6-[3-[4-(4-Fluorophenyl)piperazin-1-yl]propyl]-4,4-dimethoxy-5,6-dihydro-4H-thieno[2,3-b]thiopyran 7,7-dioxide
(64) 6-[3-[4-(4-Fluorobenzoyl)piperidino]propyl]-4,4-dimethoxy-5,6-dihydro-4H-thieno[2,3-b]thiopyran 7,7-dioxide
(65) 6-[3-[4-(2-Fluorophenyl)piperazin-1-yl]propyl]-4,4-dimethoxy-5,6-dihydro-4H-thieno[2,3-b]thiopyran 7,7-dioxide
(66) 6-[2-[4-(4-Fluorophenyl)piperazin-1-yl]ethyl]-4,4-dimethoxy-5,6-dihydro-4H-thieno[2,3-b]thiopyran 7,7-dioxide

(67) 6-[4-[4-(4-Fluorophenyl)piperazin-1-yl]butyl]-4,4-dimethoxy-5,6-dihydro-4H-thieno[2,3-b]thiopyran 7,7-dioxide
(68) 4,4-Dimethoxy-6-[3-[4-(2-pyridyl)piperazin-1-yl]propyl]-5,6-dihydro-4H-thieno[2,3-b]thiopyran 7,7-dioxide
(69) 6-[3-[4-(4-Fluorophenyl)piperazin-1-yl]propyl]-5,6-dihydro-4H-thieno[2,3-b]thiopyran-4-spiro-2'-(1',3'-dioxane) 7,7-dioxide
(70) 6-[3-[4-(4-Fluorobenzoyl)piperidino]propyl]-5,6-dihydro-4H-thieno[2,3-b]thiopyran-4-spiro-2'-(1',3'-dioxane) 7,7-dioxide
(71) 6-[3-[4-(2-Fluorophenyl)piperazin-1-yl]propyl]-5,6-dihydro-4H-thieno[2,3-b]thiopyran-4-spiro-2'-(1',3'-dioxane) 7,7-dioxide
(72) 6-[2-[4-(4-Fluorophenyl)piperazin-1-yl]ethyl]-5,6-dihydro-4H-thieno[2,3-b]thiopyran-4-spiro-2'-(1',3'-dioxane) 7,7-dioxide
(73) 6-[4-[4-(4-Fluorophenyl)piperazin-1-yl]butyl]-5,6-dihydro-4H-thieno[2,3-b]thiopyran-4-spiro-2'-(1',3'-dioxane) 7,7-dioxide
(74) 6-[3-[4-(2-Pyridyl)piperazin-1-yl]propyl]-5,6-dihydro-4H-thieno[2,3-b]thiopyran-4-spiro-2'-(1',3'-dioxane) 7,7-dioxide
(75) 6-[3-[4-[4-Fluorophenyl)piperazin-1-yl]propyl]-5,6-dihydro-4H-thieno[2,3-b]thiopyran-4-spiro-2'-(1',3'-dithiorane) 7,7-dioxide
(76) 6-[3-[4-(4-Hydroxyphenyl)piperazin-1-yl]propyl]-5,6-dihydro-4H-thieno[2,3-b]thiopyran-4-spiro-2'-(1',3'-dithiorane) 7,7-dioxide
(77) 6-[3-[4-(4-Fluorobenzoyl)piperidino]propyl]-5,6-dihydro-4H-thieno[2,3-b]thiopyran-4-spiro-2'-(1',3'-dithiorane) 7,7-dioxide
(78) 4,4-Bis(ethylthio)-6-[3-[4-(4-fluorophenyl)piperazin-1-yl]propyl]-5,6-dihydro-4H-thieno[2,3-b]thiopyran 7,7-dioxide
(79) 6-[3-[4-(4-Hydroxyphenyl)piperazin-1-yl]propyl]-5,6-dihydro-4H-thieno[2,3-b]thiopyran-4-one 7,7-dioxide
(80) 6-[3-[4-(4-Fluorobenzoyl)piperidino]propyl]-5,6-dihydro-4H-thieno[2,3-b]thiopyran-4-one 7,7-dioxide
(81) 6-[3-[4-(4-Fluorophenyl)piperazin-1-yl]propyl]-4-hydroxyimino-5,6-dihydro-4H-thieno[2,3-b]thiopyran 7,7-dioxide
(82) 4-Hydroxyimino-6-[3-[4-(4-hydroxyphenyl)piperazin-1-yl]propyl]-5,6-dihydro-4H-thieno[2,3-b]thiopyran 7,7-dioxide
(83) 6-[3-[4-(4-Fluorobenzoyl)piperidino]propyl]-4-hydroxyimino-5,6-dihydro-4H-thieno[2,3-b]thiopyran 7,7-dioxide
(84) 6-[3-[4-(4-Fluorophenyl)piperazin-1-yl]propyl]-4-hydroxy-5,6-dihydro-4H-thieno[2,3-b]thiopyran 7,7-dioxide
(85) 4-Hydroxy-6-[3-[4-(4-hydroxyphenyl)piperazin-1-yl]propyl]-5,6-dihydro-4H-thieno[2,3-b]thiopyran 7,7-dioxide
(86) 6-[3-[4-(4-Fluorobenzoyl)piperidino]propyl]-4-hydroxy-5,6-dihydro-4H-thieno[2,3-b]thiopyran 7,7-dioxide
(87) 6-[3-[4-(2-Fluorophenyl)piperazin-1-yl]propyl]-4-hydroxy-5,6-dihydro-4H-thieno[2,3-b]thiopyran 7,7-dioxide
(88) 6-[2-[4-(4-Fluorophenyl)piperazin-1-yl]ethyl]-4-hydroxy-5,6-dihydro-4H-thieno[2,3-b]thiopyran 7,7-dioxide
(89) 6-[4-[4-(4-Fluorophenyl)piperazin-1-yl]butyl]-4-hydroxy-5,6-dihydro-4H-thieno[2,3-b]thiopyran 7,7-dioxide
(90) 4-Hydroxy-6-[3-[4-(2-pyridyl)piperazin-1-yl]propyl]-5,6-dihydro-4H-thieno[2,3-b]thiopyran 7,7-dioxide
(91) 6-[3-[4-(4-Fluorophenyl)piperazin-1-yl]propyl]-4-methoxy-5,6-dihydro-4H-thieno[2,3-b]thiopyran 7,7-dioxide
(92) 6-[3-[4-(4-Hydroxyphenyl)piperazin-1-yl]propyl]-4-methoxy-5,6-dihydro-4H-thieno[2,3-b]thiopyran 7,7-dioxide
(93) 6-[3-[4-(4-Fluorobenzoyl)piperidino]propyl]-4-methoxy-5,6-dihydro-4H-thieno[2,3-b]thiopyran 7,7-dioxide
(94) 6-[3-[4-(2-Fluorophenyl)piperazin-1-yl]propyl]-4-methoxy-5,6-dihydro-4H-thieno[2,3-b]thiopyran 7,7-dioxide
(95) 4-Ethoxy-6-[3-[4-(4-fluorophenyl)piperazin-1-yl]propyl]-5,6-dihydro-4H-thieno[2,3-b]thiopyran 7,7-dioxide
(96) 4-Benzyloxy-6-[3-[4-(4-fluorophenyl)piperazin-1-yl]propyl]-5,6-dihydro-4H-thieno[2,3-b]thiopyran 7,7-dioxide
(97) 4-Benzyloxy-6-[3-[4-(4-hydroxyphenyl)piperazin-1-yl]propyl]-5,6-dihydro-4H-thieno[2,3-b]thiopyran 7,7-dioxide
(98) 4-Benzyloxy-6-[3-[4-(4-fluorobenzoyl)piperidino]propyl]-5,6-dihydro-4H-thieno[2,3-b]thiopyran 7,7-dioxide
(99) 6-[3-(4-(4-Fluorophenyl)piperazin-1-yl]propyl]-4H-thieno[2,3-b]thiopyran 7,7-dioxide
(100) 6-[3-[4-(4-Hydroxyphenyl)piperazin-1-yl]propyl]-4H-thieno[2,3-b]thiopyran 7,7-dioxide
(101) 6-[3-[4-(4-Fluorobenzoyl)piperidino]propyl]-4H-thieno[2,3-b]thiopyran 7,7-dioxide
(102) 6-[3-[4-(4-Fluorophenyl)piperazin-1-yl]propyl]-5,6-dihydro-4H-thieno[2,3-b]thiopyran 7,7-dioxide
(103) 6-[3-[4-(4-Hydroxyphenyl)piperazin-1-yl]propyl]-5,6-dihydro-4H-thieno[2,3-b]thiopyran 7,7-dioxide
(104) 6-[3-[4-(4-Fluorobenzoyl)piperidino]propyl]-5,6-dihydro-4H-thieno[2,3-b]thiopyran 7,7-dioxide
(105) 2-[3-[4-(4-Hydroxyphenyl)piperazin-1-yl]propyl]-4H-1-benzothiopyran-4-spiro-2'-(1',3'-dioxorane) 1,1-dioxide
(106) 2-[2-[4-(4-Fluorophenyl)piperazin-1-yl]ethyl]-4H-1-benzothiopyran-4-spiro-2'-(1',3'-dioxorane) 1,1-dioxide
(107) 2-[3-[4-(4-Fluorophenyl)piperazin-1-yl]propyl]-4H-1-benzothiopyran-4-spiro-2'-(1',3'-dioxane) 1,1-dioxide
(108) 2-[3-[4-(4-Hydroxyphenyl)piperazin-1-yl]propyl]-4H-1-benzothiopyran-4-spiro-2'-(1',3'-dioxane) 1,1-dioxide
(109) 2-[2-[4-(4-Fluorophenyl)piperazin-1-yl]ethyl]-4H-1-benzothiopyran-4-spiro-2'-(1',3'-dioxane) 1,1-dioxide
(110) 6-[3-[4-(4-Fluorophenyl)piperazin-1-yl]propyl]-4H-thieno[2,3-b]thiopyran-4-spiro-2'-(1',3'-dioxorane) 7,7-dioxide
(111) 6-[3-[4-(4-Hydroxyphenyl)piperazin-1-yl]propyl]-4H-thieno [2,3-b]thiopyran-4-spiro-2'-(1',3'-dioxorane) 7,7-dioxide
(112) 6-[2-[4-(4-Fluorophenyl)piperazin-1-yl]ethyl]-4H-thieno[2,3-b]thiopyran-4-spiro-2'-(1',3'-dioxorane) 7,7-dioxide
(113) 6-[3-[4-(4-Fluorophenyl)piperazin-1-yl]propyl]-4H-thieno[2,3-b]thiopyran-4-spiro-2'-(1',3'-dioxane) 7,7-dioxide
(114) 6-[3-[4-(4-Hydroxyphenyl)piperazin-1-yl]propyl]-4H-thieno[2,3-b]thiopyran-4-spiro-21'-(1',3'-dioxane) 7,7-dioxide
(115) 6-[2-[4-(4-Fluorophenyl)piperazin-1-yl]ethyl]-4H-thieno[2,3-b]thiopyran-4-spiro-2'-(1',3'-dioxane) 7,7-dioxide The chemical structures and characteristics of the compounds obtained in the examples are listed in Tables 1–7. In the tables, the values of NMR are those measured in $CDCl_3$ using TMS as the internal standard, unless otherwise indicated.

Test Examples

The anti-serotonin (5-HT) action and the anti-$\alpha_1$ action of the compounds of the present invention were examined according to the following test methods. The results obtained for typical compounds are shown in Table 8.

(1) Anti-serotonin action (Anti-5-HT action)

The superior mesenteric artery of each Hartley male guinea pig (body weight: 300–500 g) was excised. A preparation cut in a helical form was suspended under 0.3 g load in a Magnus cylinder filled with the Tyrode solution which had been aerated with a gas mixture of 95% $O_2$+5% $CO_2$ and maintained at 37° C. Using an isometric transducer ("UL-10", manufactured by SHINKOH K.K.) and a pressure preamplifier ("DSA-605A", manufactured by SHINKOH K.K.), variations in tension were measured. The isometric tensions were recorded on a pen-writing recorder ("VP-6537A", manufactured by NATIONAL K.K.). Taking the contraction induced by $10^{-5}$ M serotonin (5-HT) as 100%, the percent contractions in the presence of each test drug at $10^{-8}$ and $10^{-7}$ M were determined as anti-5-HT action.

(2) Anti-$\alpha_1$ action

The thoracic aorta of each Hartley male guinea pig (body weight: 300–500 g) was excised. A preparation cut in a helical form was suspended under 1 g load in a Magnus cylinder filled with the Tyrode solution which had been aerated with a gas mixture of 95% $O_2$+5% $CO_2$ and maintained at 37° C. Using an isometric transducer ("TB-612J", manufactured by NIHON KOHDEN) and a pressure preamplifier ("AP-620G", manufactured by NIHON KOHDEN), variations in tension were measured. The isometric tensions were recorded on a thermal pen-writing recorder ("WT-647G", manufactured by NIHON KOHDEN).

Taking the tonic contraction induced by $10^{-5}$ M norepinephrine (NE) as 100%, the percent contractions upon addition of each test drug at $10^{-8}$ and $10^{-7}$ M were determined as anti-$\alpha_1$ action.

TABLE 1

| Compound No. | Chemical Structure | Characteristics m.p. (Solvent for recrystallization) | NMR* (δ ppm/400 MHz) | IR (cm$^{-1}$) ( ) Measurement method |
|---|---|---|---|---|
| 1 | 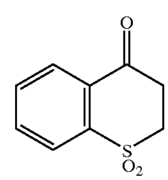 | Colorless prisms 131.0–132.5° C. (Ethanol) | 3.42(2H, t, J=6.4Hz), 3.70(2H, t, J= 6.4Hz), 7.74(1H, dt, J=1.2Hz, 7.6Hz), 7.82(1H, dt, J=1.2Hz, 7.6Hz), 8.01 (1H, dd, J=1.2Hz, 7.6Hz), 8.12(1H, dd, J=1.2Hz, 7.6Hz) | (KBr) 3084, 2990, 1680 1586, 1571, 1448 1403, 1319, 1294 1245, 1190,1158 1132, 1082, 862 788, 742, 666 |
| 2 | 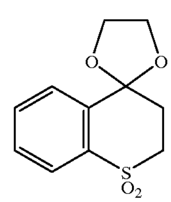 | Colorless prisms 95.5–101.0° C. (Ethyl acetate-diipropyl ether) | 2.66(2H, m), 3.63(2H, m), 4.15(2H, m), 4.24(2H, m), 7.53~7.59(3H, m), 7.89(1H, m) | (KBr) 2886, 1479, 1444 1319, 1152, 1118 1057, 1023, 980 946, 904, 879 854, 781, 758 |
| 3 | 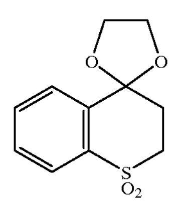 | Colorless prisms 89.0–91.0° C. (Ethyl acetate-hexane) | 1.92(1H, m), 2.13(2H, m), 2.32(1H, m), 2.34(1H, dd, J=2.2Hz, 14.6Hz), 2.63 (1H, dd, J=2.6Hz, 14.6Hz), 3.57~ 3.75(3H, m), 4.06~4.23(3H, m), 4.35(1H, m), 7.53~7.60(3H, m), 7.91(1H, dd, J=2.2Hz, 5.9Hz) | (KBr) 2966, 1479, 1450 1291, 1244,1142 1048, 982, 945 860, 770, 745, 692, 670, 652 |
| 4 | 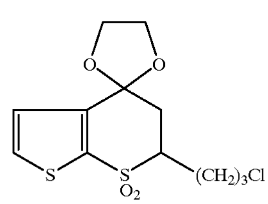 | Colorless prisms 108.0–109.5° C. (Ethyl acetate-hexane) | 1.92(1H, m), 2.10(2H, m), 2.29(1H, m), 2.32(1H, dd, J=2.2Hz, 14.7Hz), 2.67 (1H, dd, J=12.1Hz, 14.7Hz), 3.57~ 3.72(3H, m), 4.05~4.18(3H, m), 4.26(1H, m), 7.01(1H, d, J=5.1Hz), 7.54(1H, d, J=5.1Hz) | (KBr) 3106, 2959, 2895 1447, 1416,1324 1299, 1280, 1262 1142, 1095, 1059 1026, 1008, 977 946, 750, 692 |

*: Measured in $CDCl_3$ with TMS as an internal standard unless otherwise specifically indicated.

TABLE 2

| Compound No. | Chemical Structure | Characteristics m.p. (Solvent for recrystallization) | NMR* (δ ppm/400 MHz) | IR (cm⁻¹) ( ) Measurement method |
|---|---|---|---|---|
| 5 | (chromanone sulfone with (CH₂)₃Cl) | Colorless oil | 1.89(1H, m), 2.08(2H, m), 2.38(1H, m), 3.32(2H, m), 3.61(2H, m), 3.68(1H, m), 7.74(1H, dt, J=0.7Hz, 7.6Hz), 7.83(1H, dt, J=1.1Hz, 7.6Hz), 8.04(1H, dd, J=1.1Hz, 7.6Hz), 8.11(1H, dd, J=0.7Hz, 7.6Hz) | (film) 2961, 1694, 1589 1570, 1444, 1304 1237, 1153, 1125 1049, 758 |
| 6 | (chromanol sulfone with (CH₂)₃Cl) | Colorless needles 100.5–102.0° C. (Ethyl acetate-hexane) | 1.88(1H, m), 2.08(2H, m), 2.30(2H, m), 2.46(1H, d, J=8.8Hz), 2.57(1H, m), 3.27(1H, m), 3.63(2H, m), 4.91(1H, m), 7.50(1H, t, J=7.6Hz), 7.60(1H, t, J=7.6Hz), 7.70(1H, t, J=7.6Hz), 7.89(1H, d, J=7.6Hz) | (KBr) 3452, 1475, 1446 1422, 1316, 1278 1262, 1131, 1096 1044, 766, 746 720 |
| 7 | (dioxolane-bromo-sulfone with (CH₂)₃Cl) | Colorless prisms 127.0–129.5° C. (Ethyl acetate-hexane) | 2.03~2.24(3H, m), 2.43(1H, m), 3.67(2H, m), 4.10(1H, m), 4.17~4.30(3H, m), 4.42(1H, m), 4.48(1H, d, J=3.0Hz), 7.60~7.64(3H, m), 7.94(1H, m) | (KBr) 2960, 2891, 1476 1454, 1442, 1303 1272, 1248, 1144 1129, 1050, 1018 981, 952, 762 706 |
| 8 | (dioxolane-sulfone with (CH₂)₃-N-phenylpiperazine) | Colorless prisms 115.5–119.5° C. (Ethyl acetate-hexane) | 1.67~1.91(3H, m), 2.28(1H, m), 2.37(1H, dd, J=2.4Hz, 14.6Hz), 2.49(2H, m), 2.56~2.69(5H, m), 3.21(4H, m), 3.74(1H, m), 4.05~4.24(3H, m), 4.35(1H, m), 6.85(1H, t, J=7.3Hz), 6.93(2H, d, J=7.9Hz), 7.25(2H, m), 7.51~7.61(3H, m), 7.92(1H, m) | (KBr) 2942, 2824, 1600 1503, 1446, 1381 1292, 1233, 1140 1048, 948, 757 697 |

*: Measured in CDCl₃ with TMS as an internal standard unless otherwise specifically indicated.

TABLE 3

| Compound No. | Chemical Structure | Characteristics m.p. (Solvent for recrystallization) | NMR* (δ ppm/400 MHz) | IR (cm⁻¹) ( ) Measurement method |
|---|---|---|---|---|
| 9 | (dioxolane-sulfone with (CH₂)₃-N-4-phenylpiperidine) | Yellow oil | 1.55~1.91(7H, m), 2.08(2H, m), 2.26(1H, m), 2.40(1H, dd, J=2.4Hz, 14.6Hz), 2.43~2.55(3H, m), 2.60(1H, dd, J=12.6Hz, 14.6Hz), 3.07(2H, m), 3.73(1H, m), 4.05~4.24(3H, m), 4.35(1H, m), 7.16~7.32(5H, m), 7.56(3H, m), 7.92(1H, m) | (film) 2935, 2769, 1601 1494, 1441, 1296 1141, 1049, 993 947, 867, 760 701 |

TABLE 3-continued

| Compound No. | Chemical Structure | Characteristics m.p. (Solvent for recrystallization) | NMR* (δ ppm/400 MHz) | IR (cm$^{-1}$) ( ) Measurement method |
|---|---|---|---|---|
| 10 | 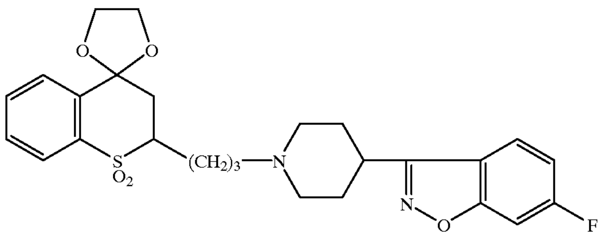 | Yellow oil | 1.67~1.94(3H, m), 2.02~2.24(6H, m), 2.29(1H, m), 2.38(1H, dd, J=2.4Hz, 14.6Hz), 2.50(2H, m), 2.62(1H, dd, J=12.6Hz, 14.6Hz), 2.99~3.15(3H, m), 3.79(1H, m), 4.06~4.24(3H, m), 4.36(1H, m), 7.03(1H, dt, J=2.1Hz, 8.9Hz), 7.23(1H, dd, J=2.1Hz, 8.5Hz), 7.53~7.60(3H, m), 7.69(1H, dd, J=5.1Hz, 8.7Hz), 7.93(1H, m) | (film) 2945, 2809, 1614 1515, 1494, 1442 1416, 1295, 1273 1141, 1049, 993 956, 840, 816 751 |
| 11 | 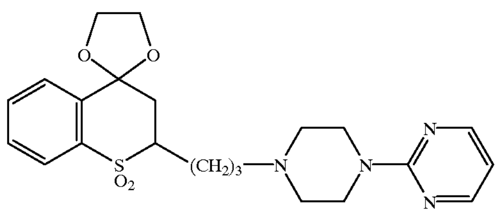 | Pale yellow prisms 137.0–139.5° C. (Ethyl acetate-hexane) | 1.68~1.91(3H, m), 2.28(1H, m), 2.38(1H, dd, J=2.4Hz, 14.6Hz), 2.47(2H, t, J=7.3Hz), 2.52(4H, m), 2.61(1H, dd, J=12.6Hz, 14.6Hz), 3.75(1H, m), 3.84(4H, m), 4.05~4.24(3H, m), 4.36(1H, m), 6.47(1H, t, J=4.7Hz), 7.51~7.61(3H, m), 7.92(1H, m), 8.30(2H, d, J=4.7Hz) | (KBr) 2890, 1586, 1549 1499, 1430, 1392 1360, 1286, 1145 1049, 999, 984 949, 802, 758 |
| 12 | 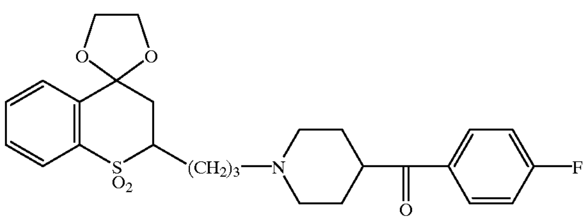 | Pale yellow prisms 115.0–118.0° C. (Ethyl acetate) | 1.66~1.91(7H, m), 2.12(2H, m), 2.24(1H, m), 2.37(1H, dd, J=2.4Hz, 14.5Hz), 2.45(2H, m), 2.60(1H, dd, J=12.6Hz, 14.5Hz), 3.01(2H, m), 3.20(1H, quint, J=7.5Hz), 3.73(1H, m), 4.05~4.24(3H, m), 4.35(1H, m), 7.13(2H, m), 7.51~7.60(3H, m), 7.89~8.00(3H, m) | (KBr) 2948, 2774, 1684 1599, 1508, 1444 1409, 1378, 1301 1227, 1134, 1047 982, 944, 853 766, 747, 676 |

*: Measured in CDCl$_3$ with TMS as an internal standard unless otherwise specifically indicated.

TABLE 4

| Compound No. | Chemical Structure | Characteristics m.p. (Solvent for recrystallization) | NMR* (δ ppm/400 MHz) | IR (cm$^{-1}$) ( ) Measurement method |
|---|---|---|---|---|
| 13 | 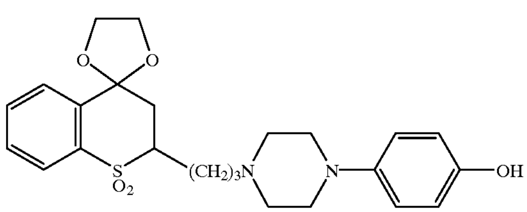 | Pale yellow prisms 178.5–183.0° C. (Ethyl acetate-hexane) | 1.75(1H, m), 1.82(2H, m), 2.27(1H, m), 2.37(1H, dd, J=2.3Hz, 14.6Hz), 2.49(2H, t, J=7.3Hz), 2.56(5H, m), 3.09(4H, m), 3.73(1H, m), 4.04~4.22(3H, m), 4.34(1H, m), 6.75(2H, d, J=8.9Hz), 6.84(2H, d, J=8.9Hz), 7.53~7.59(3H, m), 7.92(1H, dd, J=2.8Hz, 6.2Hz) | (KBr) 2948, 2888, 2836 1513, 1453, 1442 1319, 1285, 1258 1232, 1141, 1049 998, 943, 914 829, 766 |
| 14 | 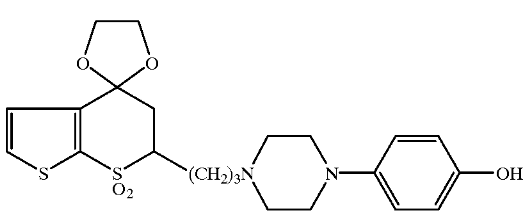 | Colorless powder 205° C. (Decomposed) (—) | 1.70~1.85(3H, m), 2.25(1H, m), 2.35(1H, dd, J=2.1Hz, 14.7Hz), 2.62(2H, m), 2.61~2.67(5H, m), 3.09(4H, m), 3.73(1H, m), 4.03~4.17(3H, m), 4.26(1H, m), 6.75(2H, d, J=9.9Hz), 6.84(2H, d, J=9.9Hz), 7.01(1H, d, J=5.1Hz), 7.53(1H, d, J=5.1Hz) | (KBr) 2949, 2884, 2833 1514, 1456, 1310 1286, 1260, 1236 1143, 1018, 996 948, 913, 825 754, 719, 675 |

TABLE 4-continued

| Compound No. | Chemical Structure | Characteristics m.p. (Solvent for recrystallization) | NMR* (δ ppm/400 MHz) | IR (cm⁻¹) ( ) Measurement method |
|---|---|---|---|---|
| 15 | (structure: thieno-fused dioxolane spiro sulfone with -(CH₂)₃-piperazine-phenyl) | Colorless powder 112.5–114.5° C. (Ethyl acetate-hexane) | 1.68~1.90(3H, m), 2.25(1H, m), 2.35(1H, dd, J=2.2Hz, 14.7Hz), 2.48(2H, m), 2.59~2.69(5H, m), 3.21(4H, m), 3.74(1H, m), 4.06 (1H, m), 4.14(2H, m), 4.26(1H, m), 6.84(1H, t, J=7.33Hz), 6.92 (2H, d, J=7.9Hz), 7.01(1H, d, J=5.1Hz), 7.26(2H,m), 7.53(1H, d, J=5.1Hz) | (KBr) 2824, 1599, 1503, 1455, 1411, 1381 1304, 1228, 1193 1140, 1054, 1028 948, 850, 757 694 |
| 16 | (structure: benzo-fused dioxolane spiro sulfone with -(CH₂)₃-piperazine-C₆H₄-F) | Colorless needles 153.5–156.0° C. (Ethyl acetate-hexane) ---------- (Monomaleate) Colorless prisms 145.0–148.5° C. (Acetonitrile-ethyl acetate) | 1.74(1H, m), 1.82(2H, m), 2.28 (1H, m), 2.37(1H, dd, J=2.3Hz, 14.6Hz), 2.49(2H, t, J=7.2Hz), 2.58~2.64(5H, m), 3.13(4H, m), 3.74(1H, m), 4.05~4.22(3H, m), 4.35(1H, m), 6.88(2H, m), 6.95 (2H, m), 7.52~7.60(3H, m), 7.91(1H, dd, J=2.9Hz, 6.1Hz) | (KBr) 2946, 2897, 2829 1511, 1452, 1292 1217, 1140, 1048 1000, 948, 838 766, 720, 708 680 |

*: Measured in CDCl₃ with TMS as an internal standard unless otherwise specifically indicated.

TABLE 5

| Compound No. | Chemical Structure | Characteristics m.p. (Solvent for recrystallization) | NMR* (δ ppm/400 MHz) | IR (cm⁻¹) ( ) Measurement method |
|---|---|---|---|---|
| 17 | (structure: benzo-fused dioxolane spiro sulfone with -(CH₂)₂-piperazine-C₆H₄-F) | Colorless needles 125.0–126.5° C. (Ethyl acetate-hexane) | 1.85(1H, m), 2.42~2.55(2H, m), 2.58~2.70(7H, m), 3.12 (4H, m), 3.90(1H, m), 4.08 (1H, m), 4.18(2H, m), 4.33 (1H, m), 6.88(2H, m), 6.95 (2H, m), 7.54~7.60(3H, m), 7.91(1H, m) | (KBr) 2821, 1511, 1455 1298, 1230, 1136 1050, 992,978 942, 929, 817 770, 751 |
| 18 | (structure: thieno-fused dioxolane spiro sulfone with -(CH₂)₃-piperazine-C₆H₄-F) | Pale yellow prisms 138.5–140.0° C. (Ethyl acetate-hexane) ---------- (mono p-Toluene-sulfoniate) Colorless powder 199.5–202.0° C. (Methanol-ethyl ether) | 1.68~1.87(3H, m), 2.25(1H, m), 2.35(1H, dd, J=2.2Hz, 14.6Hz), 2.48(2H, m), 2.60~ 2.68(5H, m), 3.12(4H, m), 3.74(1H, m), 4.03~4.17(3H, m), 4.27(1H, m), 6.87(2H, m), 6.95(2H, m), 7.01(1H, d, J=5.1Hz), 7.54(1H, d, J= 5.1Hz) | (KBr) 2944, 2830, 1509 1452, 1413, 1384 1298, 1257, 1237 1138, 1024, 986 947, 906, 828 749, 692 |
| 19 | (structure: 4-oxo-thiochromanone sulfone with -(CH₂)₃-piperazine-C₆H₄-F) | Yellow prisms 120.0–122.5° C. (Ethanol) | 1.69~1.84(3H, m), 2.32(1H, m), 2.46(2H, m), 2.58(4H, m), 3.10(4H, m), 3.28(1H, dd, J=10.1Hz, 17.6Hz), 3.37(1H, dd, J=3.8Hz, 17.6Hz), 3.71 (1H, m), 6.86(2H, m), 6.95 (2H, m), 7.74(1H, t, J= 7.7Hz), 7.83(1H, t, J=7.7Hz), 8.05(1H, d, J=7.7Hz), 8.11 (1H,d, J=7.7Hz) | (KBr) 2932, 2814, 1693 1511, 1455, 1306 1282, 1226, 1153 1124, 1003, 922 832, 817, 779 748, 720 |

TABLE 5-continued

| Compound No. | Chemical Structure | Characteristics m.p. (Solvent for recrystallization) | NMR* (δ ppm/400 MHz) | IR (cm$^{-1}$) ( ) Measurement method |
|---|---|---|---|---|
| 20 | (thieno-thiopyranone with (CH$_2$)$_3$-N-piperazine-N-(4-F-phenyl), S$O_2$) | Pale yellow powder 111.5–113.0° C. (Ethyl acetate-hexane) | 1.70~1.86(3H, m), 2.31(1H, m), 2.46(2H, m), 2.58(4H, m), 3.10(4H, m), 3.23~3.27 (2H, m), 3.81(1H, m), 6.86 (2H, m), 6.95(2H, m), 7.48 (1H, d, J=5.1Hz), 7.58(1H, d, J=5.1Hz) | (KBr) 2819, 1684, 1509, 1451, 1394, 1308, 1229, 1149, 1004, 925, 817, 752, 718, 663 |

*: Measured in CDCl$_3$ with TMS as an internal standard unless otherwise specifically indicated.

TABLE 6

| Compound No. | Chemical Structure | Characteristics m.p. (Solvent for recrystallization) | NMR* (δ ppm/400 MHz) | IR (cm$^{-1}$) ( ) Measurement method |
|---|---|---|---|---|
| 21 | (dithiolane-spiro-thiochromane with (CH$_2$)$_3$N-piperazine-N-(4-F-phenyl), S$O_2$) | Colorless oil ---------- (Monomaleate) Colorless prisms 155.0–156.0° C. (Chloroform-ethyl ether) | 1.73(1H, m), 1.84(2H, m), 2.29(1H, m), 2.51(2H, t, J= 7.4Hz), 2.63(4H, m), 2.67 (1H, dd, J=1.9Hz, 15.3Hz), 3.05(1H, dd, J=2.4Hz, 15.3Hz), 3.13(4H, m), 3.39 (1H, m), 3.63(2H, m), 3.71 (2H, m), 6.88(2H, m), 6.95 (2H, m), 7.43(1H, m), 7.53 (1H, m), 7.85(1H, dd, J= 1.2Hz, 7.9Hz), 8.01(1H, dd, J=0.7Hz, 8.1Hz) | (film) 2944, 2819, 1510 1469, 1455, 1435 1292, 1233, 1148 1129, 981, 826 755, 736 |
| 22 | (N-OH oxime thiochromanone with (CH$_2$)$_3$-N-piperazine-N-(4-F-phenyl), S$O_2$) | Colorless prisms 216.0–220.0° C. (Acetonitrile) | (DMSO-d$_6$/TMS) 1.54(1H, m), 1.67(2H, m), 2.02(1H, m), 2.36(2H, t, J= 6.8Hz), 2.49(4H, m), 2.95 (1H, dd, J=10.0Hz, 18.4Hz), 3.04(4H, m), 3.42(1H, dd, J= 4.7Hz, 18.4Hz), 3.62(1H, m), 6.92(2H, dd, J=4.7Hz, 9.2Hz), 7.01(2H, t, J=8.8Hz), 7.64(1H, dt, J=1.3Hz, 7.5Hz), 7.69(1H, dt, J=1.3Hz, 7.5Hz), 7.88(1H, dd, J=1.3Hz, 7.5Hz), 8.03(1H, dd, J= 1.3Hz, 7.5Hz) | (KBr) 2831, 1511, 1456 1386, 1301, 1237 1144, 974, 925 824, 815, 755 718 |
| 23 | (4-OH thiochromane with (CH$_2$)$_3$-N-piperazine-N-(4-F-phenyl), S$O_2$) | Colorless prisms 170.0–171.0° C. (Ethanol) | 1.69~1.84(3H, m), 2.30(1H, m), 2.37(1H, m), 2.48(2H, m), 2.60~2.68(5H, m), 3.12 (4H, m), 3.26(1H, m), 4.92 (1H, dd, J=5.3Hz, 10.5Hz), 6.87(2H, m), 6.95(2H, m), 7.50(1H, t, J=7.9Hz), 7.60 (1H, t, J=7.9Hz), 7.70(1H, d, J=7.9Hz), 7.92(1H, d, J= 7.9Hz) | (KBr) 3072, 2955, 2831 1531, 1442, 1305 1248, 1132, 1062 997, 929, 812 771, 751 |
| 24 | (2H-thiochromene with (CH$_2$)$_3$-N-piperazine-N-(4-F-phenyl), S$O_2$) | Pale yellow oil | 1.73~1.85(3H, m), 2.24(1H, m), 2.44(2H, m), 2.58(4H, m), 3.10(4H, m), 3.82(1H, m), 6.16(1H, dd, J=4.6Hz, 10.5Hz), 6.68(1H, dd, J= 1.5Hz, 10.5Hz), 6.86(2H, m), 6.94(2H, m), 7.29(1H, d, J= 7.5Hz), 7.48(1H, dt, J=1.0Hz, 7.5Hz), 7.58(1H, dt, J=1.3Hz, 7.5Hz), 7.99(1H, d, J=7.5Hz) | (film) 2945, 2819, 1594 1510, 1455, 1304 1236, 1153, 1067 924, 817, 783 724, 669 |

*: Measured in CDCl$_3$ with TMS as an internal standard unless otherwise specifically indicated.

TABLE 7

| Compound No. | Chemical Structure | Characteristics m.p. (Solvent for recrystallization) | NMR* (δ ppm/400 MHz) | IR (cm$^{-1}$) ( ) Measurement method |
|---|---|---|---|---|
| 25 | 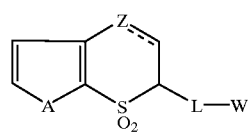 | Colorless prisms 101.0–102.5° C. (Methanol-ethyl ether) | 1.93(2H, m), 2.50(2H, t, J=7.0Hz), 2.61(4H, m), 2.70(2H, t, J=7.7Hz), 3.12(4H, m), 4.25(4H, m), 6.31 (1H, s), 6.87(2H, m), 6.95(2H, m), 7.57~7.64(3H, m), 8.00(1H, m) | (KBr) 2958, 2891, 2811 1511, 1445, 1294 1243, 1216, 1148 1054, 1019, 982 826, 782 |

*: Measured in CDCl$_3$ with TMS as an internal standard unless otherwise specifically indicated.

TABLE 8

| Compound No. | Anti-HT action (% of the control) | | Anti α$_1$ action (% of the control) | |
|---|---|---|---|---|
| | 10$^{-8}$ M | 10$^{-7}$ M | 10$^{-8}$ M | 10$^{-7}$ M |
| 8 | 57.4 | 12.0 | 91.1 | 55.5 |
| 9 | 71.8 | 9.3 | 98.7 | 71.6 |
| 14 | 41.8 | 12.3 | 100 | 95.9 |
| 16* | 39.2 | 5.5 | 94.1 | 51.5 |
| 18 | 44.8 | 8.0 | 88.6 | 44.0 |
| 23 | 52.8 | 22.5 | 100 | 90.1 |
| 25 | 18.8 | 6.1 | 95.1 | 47.8 |
| 28* | 28.4 | 13.0 | 90.8 | 32.1 |

*Monomaleate was used as the test compound.

The thiopyran derivatives (I) or (I'), or the salts thereof, of the present invention have been confirmed to exhibit a strong serotonin-2 blocking action and to be highly safe. These compounds therefore are useful as drugs utilizing their serotonin-2-recepter antagonistic action, such as drugs for the treatment of circulatory diseases such as ischemic heart disease, cerebrovascular disturbance, and peripheral circulatory disturbance. Some compounds of the present invention exhibit an α$_1$-blocking action in addition to the serptonin-2 blocking action. These compounds are useful as an antihypertensive agent with less side effects. The compounds of the present invention are therefore extremely useful as drugs for the treatment of circulatory diseases in general.

Obviously, numerous modifications and variations of the present invention are possible in light of the above teachings. It is therefore to be understood that, within the scope of the appended claims, the invention may be practiced otherwise than as specifically described herein.

What is claimed is:

1. An intermediate represented by the following formula (XVIII), (XVIII)

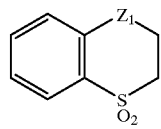

wherein A is the group —CH═CH—; L is an alkylene group which may be substituted, an alkenylene group which may be substituted, or an alkynylene group which may be substituted, wherein when L is a group which is substituted, it is substituted by one or more halogen atoms; W represents a leaving group selected from the group consisting of a halogen atom, an alkyl sulfonyloxy group, and an aryl sulfonyloxy group, and Z represents the group;

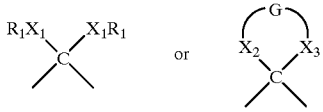

(wherein R$_1$ is an alkyl group which may be substituted, an aromatic carbocyclic group which may be substituted, or an aralkyl group which may be substituted, wherein when R$_1$ is a group which is substituted, it is substituted by one or more halogen atoms, alkyl groups, or alkoxy groups, X$_1$, X$_2$, and X$_3$ individually represent an oxygen atom or a sulfur atom, and G represents an ethylene group or a trimethylene group, of which one or more hydrogen atoms of the ethylene group or trimethylene group may be replaced by a halogen atom, alkyl group, aromatic carbocyclic group, aralkyl group, or alkylidene group).

2. An intermediate represented by the following formula (XIX), (XIX)

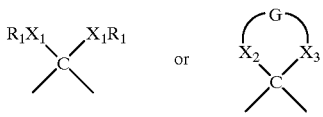

wherein Z$_1$ represents the group;

(wherein R$_1$ is an alkyl group which may be substituted, an aromatic carbocyclic group which may be substituted, or an aralkyl group which may be substituted, wherein when R$_1$ is a group which is substituted, it is substituted by one or more halogen atoms, alkyl groups, or alkoxy groups, X$_1$, X$_2$, and X$_3$ individually represent an oxygen atom or a sulfur atom, and G represents an ethylene group or a trimethylene group, of which one or more hydrogen atoms of the ethylene group or trimethylene group may be replaced by a halogen atom, alkyl group, aromatic carbocyclic group, aralkyl group, or alkylidene group).

* * * * *